(12) United States Patent
Aryev et al.

(10) Patent No.: US 6,581,012 B1
(45) Date of Patent: Jun. 17, 2003

(54) AUTOMATED LABORATORY SOFTWARE ARCHITECTURE

(75) Inventors: Michael Aryev, Weston, FL (US); Andrea L. Krensky, Miami, FL (US); Fredric W. Huls, Miramar, FL (US); Gerardo Garcia, Miami, FL (US); Bin Qin, Weston, FL (US); David J. Roach, Sunrise, FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/364,602

(22) Filed: Jul. 30, 1999

(51) Int. Cl.[7] ............................................. G06F 19/00
(52) U.S. Cl. .............................. 702/22; 709/203; 705/2
(58) Field of Search ........................ 702/108, 121–123, 702/183, 19, 21–23, 27–32, 83; 422/67; 700/1, 96, 266; 436/43; 600/368–369, 300; 705/1–3, 7–9; 709/203, 213; 235/375, 385

(56) References Cited

U.S. PATENT DOCUMENTS

| | | | | |
|---|---|---|---|---|
| 4,491,725 A | * | 1/1985 | Pritchard | 705/2 |
| 5,171,977 A | * | 12/1992 | Morrison | 235/375 |
| 5,614,415 A | | 3/1997 | Markin | 436/48 |
| 5,631,844 A | | 5/1997 | Margrey et al. | 364/496 |
| 5,793,969 A | * | 8/1998 | Kamentsky et al. | 709/213 |
| 5,841,975 A | * | 11/1998 | Layne et al. | 709/203 |
| 5,923,018 A | * | 7/1999 | Kameda et al. | 235/385 |
| 5,925,514 A | * | 7/1999 | Layne et al. | 435/5 |
| 5,930,791 A | | 7/1999 | Leu | 707/8 |
| 5,937,364 A | * | 8/1999 | Westgard et al. | 702/83 |

FOREIGN PATENT DOCUMENTS

| | | |
|---|---|---|
| EP | 0 596 205 A2 | 5/1994 |
| EP | 0676 053 B1 | 8/1997 |

OTHER PUBLICATIONS

Smith, et al., "Abbott AxSYM Random and Continuous Access Immunoassay System for Improved Workflow in the Clinical Laboratory", *Clin. Chem.*, vol. 39, No. 10, pp 2063–2069 (1993).

* cited by examiner

*Primary Examiner*—Marc S. Hoff
*Assistant Examiner*—Mohamed Charioui
(74) *Attorney, Agent, or Firm*—Birch, Stewart, Kolasch & Birch, LLP; Mitchell E. Alter

(57) ABSTRACT

An integrated clinical laboratory software system for testing a specimen. At least one specimen processing module is advantageously provided, each for performing particular predetermined tests on the specimen. Integrated work flow automation programming communicates with any of the plurality of specimen processing modules. The specimen processing modules can include instrument hardware and embedded process control software. The work flow automation programming includes request processing programming for processing a user request for any of the tests which are available to be performed by the specimen processing modules, and also includes functional control programming which provides functional control of any of the plurality of specimen processing modules for performing any of the tests, and which further includes result data management programming provides processing of test result data of any of the tests.

23 Claims, 28 Drawing Sheets

PRE-ANALYTICAL PROCESS

ORDER ENTRY

SPECIMEN COLLECTION & LABELING

SPECIMEN RECEIPT

SPECIMEN SORTING

ALIQUOTING

SPECIMEN DELIVERY

WORK LOAD BALANCING

REFLEX TESTING

ANALYTICAL PROCESS

Q.C. ANALYSIS

ANALYZER CHECKS

SPECIMEN IDENTIFICATION

SAMPLE ANALYSIS

SAMPLE PREPARATION

REPEATS

POST-ANALYTICAL PROCESS

TEST DATA REVIEW

RESULT VERIFICATION

QA STATISTICAL ANALYSIS

INSURANCE CLAIMS

RESULT DATA STORAGE

SPECIMEN STORAGE

SPECIMEN RETRIEVAL

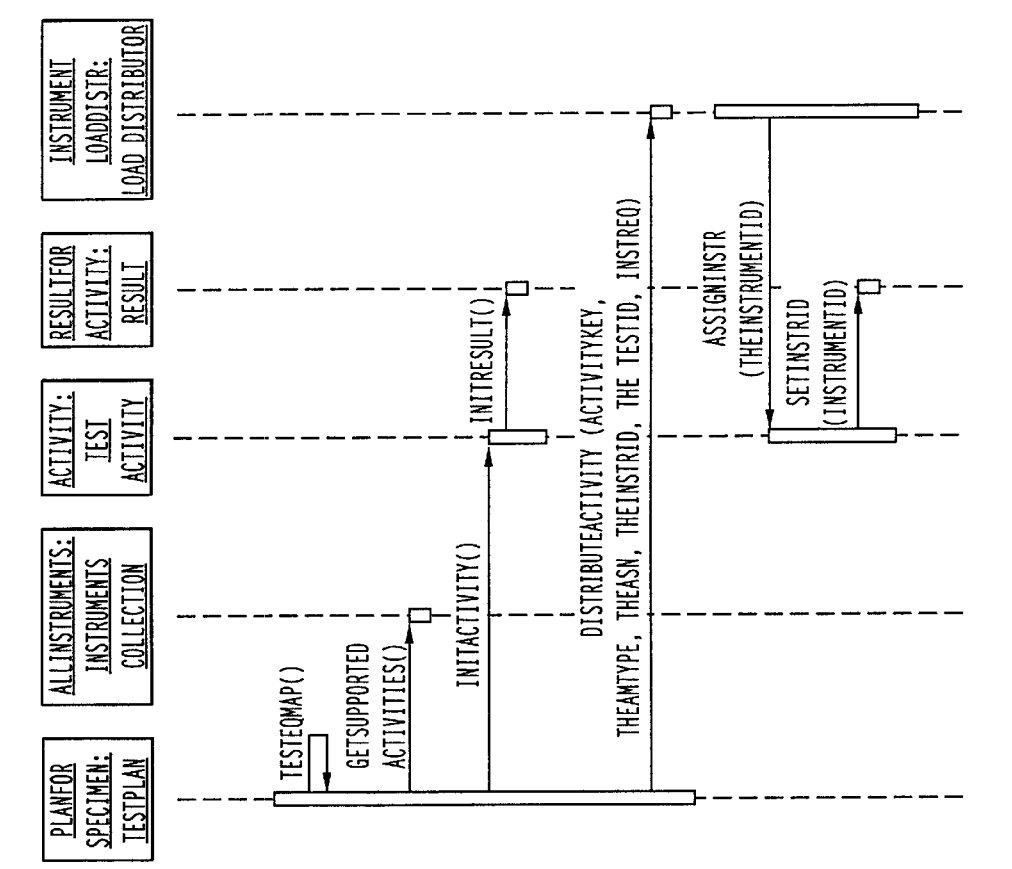

FIG. 14

THIS SCENARIO ILLUSTRATES THE SYSTEM MAPPING A REQUESTED TEST INTO A TEST ACTIVITY THAT IS RUN ON AN INSTRUMENT. THE REQUESTOR OF THE TEST DID NOT SPECIFY A PARTICULAR INSTRUMENT.

THE TESTEQMAP() OPERATION MAPS A SET OF REQUESTED TESTS INTO TESTACTIVITIES.

THE TESTPLAN FIRST DETERMINES WHAT TEST ACTIVITIES ARE AVAILABLE IN THE SYSTEM. USING THIS INFORMATION A TEST ACTIVITY THAT MEETS THE REQUIREMENTS OF THE DESIRED TEST IS CREATED, AND ITS CORRESPONDING RESULT IS INITIALIZED.

THE TESTPLAN NEXT INFORMS THE LOAD DISTRIBUTION PORTION OF THE SYSTEM ABOUT THE TEST ACTIVITY. THE LOAD DISTRIBUTOR IS RESPONSIBLE FOR ASSIGNING THE TEST ACTIVITY TO THE "OPTIMAL" INSTRUMENT, AND FOR INITIATING THE DELIVERY OF THE SPECIMEN TO THE INSTRUMENT. THE SCENARIOS FOR THE LOAD DISTRIBUTOR (E.G. THE SPECIMEN IS ALREADY IN THE REALM OF THE SYSTEM, THE SPECIMEN HAS NOT YET BEEN SEEN IN THE SYSTEM, ETC.) ARE SHOWN IN ANOTHER USE CASE.

AT SOME LATER TIME, THE TEST ACTIVITY IS ASSIGNED TO AN INSTRUMENT IN THE COMPLEX. THE LOAD DISTRIBUTION PORTION OF THE SYSTEM INFORMS THE TEST ACTIVITY OF WHAT INSTRUMENT IT HAS BEEN ASSIGNED TO. THE TEST ACTIVITY, IN TURN, INFORMS ITS CORRESPONDING RESULT OF WHICH INSTRUMENT WILL BE PRODUCING THE DATA IT WILL PROCESS.

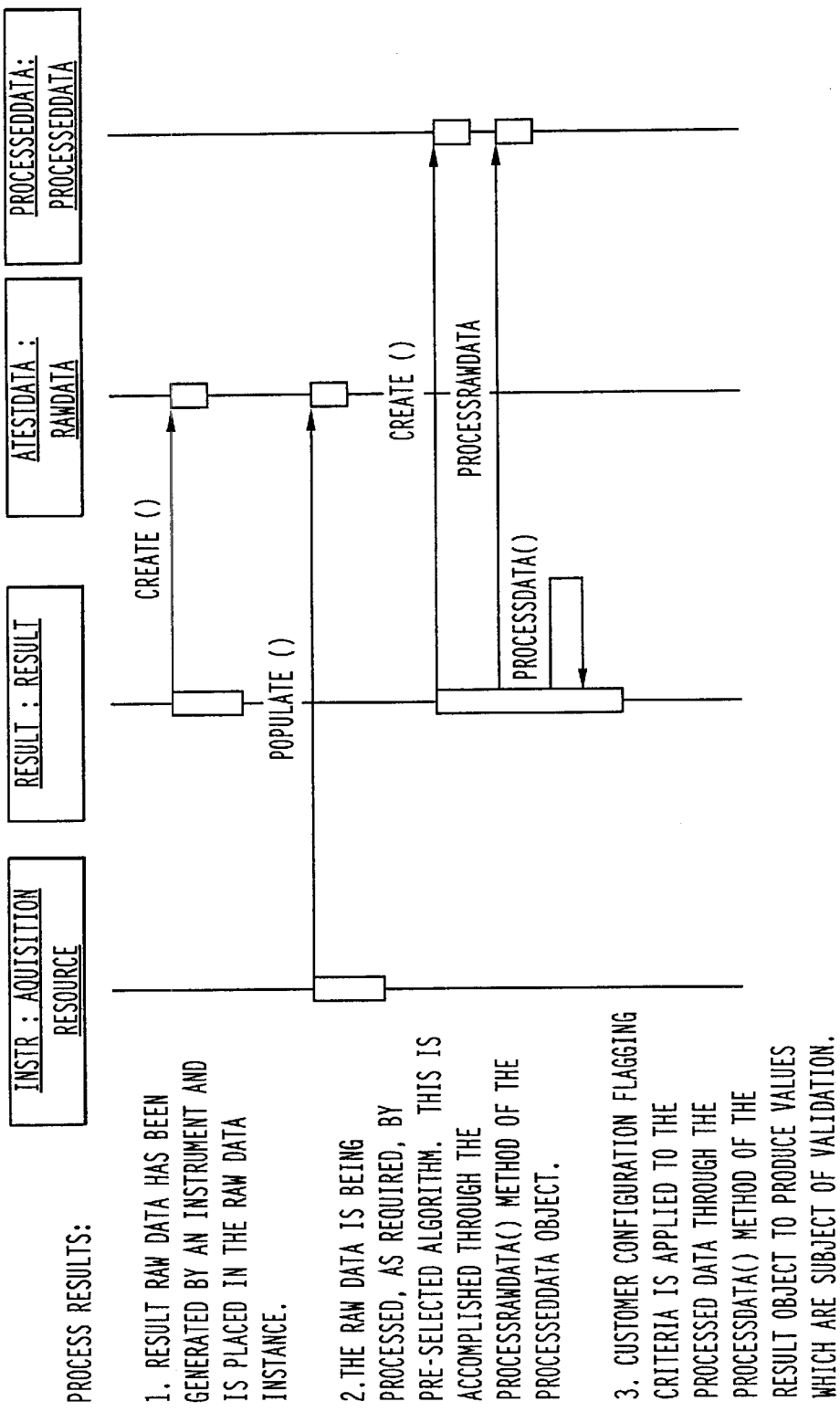

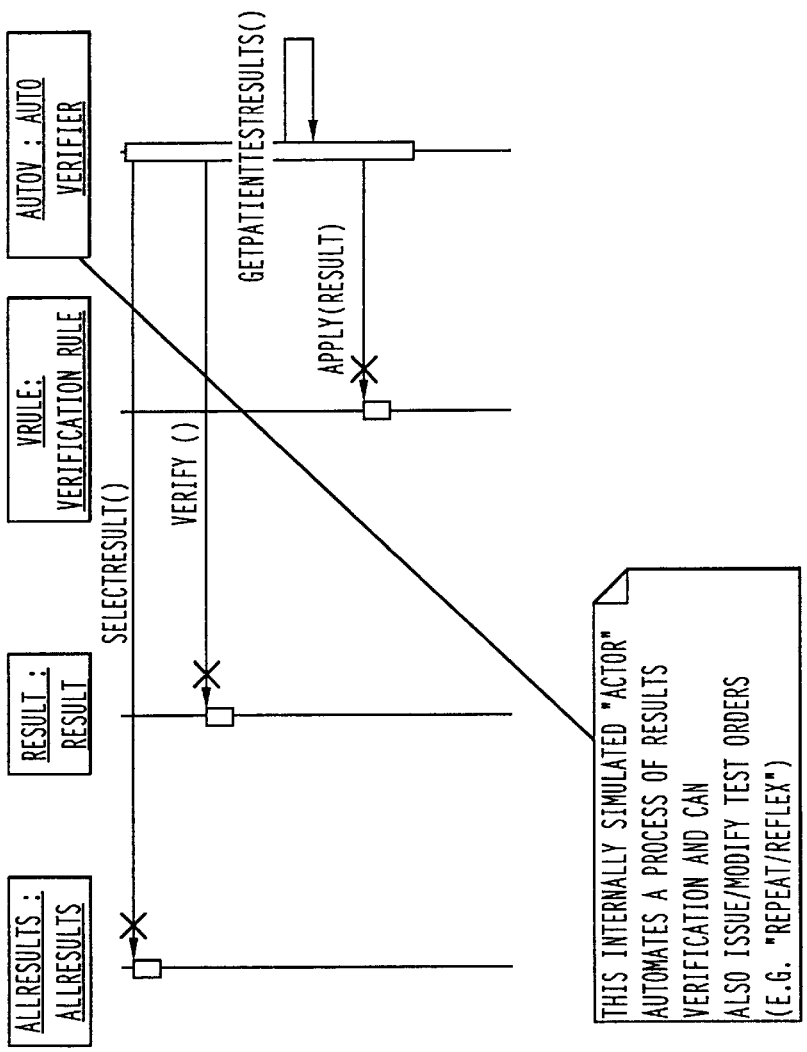

FIG. 23

THIS SCENARIO ILLUSTRATES THE
VERIFICATION OF RESULTS ASSOCIATED WITH PATIENT
TEST RESULTS. THE VERIFICATION RULES CAN BE
APPLIED AUTOMATICALLY BY THE SYSTEM OR THE OPERATOR
CAN SELECT TO APPLY THE CONFIGURED VERIFICATION
RULES MANUALLY.

1. SELECT A RESULT WHICH IS READY TO BE VERIFIED.

2. ON THE VERIFICATION REQUEST THE RESULT APPLIES
   ITS SELECTED CRITERIA TO THE PROCESSED DATA.

3. TO COMPLETE VERIFICATION, PREVIOUS TEST RESULTS
   MAY NEED TO BE CONSULTED WITHIN A CONTEXT OF EXISTING
   VERIFICATION RULES. THIS IS REPRESENTED BY THE
   GETPATIENTTEST RESULTS () OPERATION. THE DETAILS OF
   THIS ARE SHOWN IN THE GETPATIENTTESTRESULTS SCENARIO
   UNDER THE GETTESTRESULT USE CASE.

4. USE THE METHOD APPLY() TO APPLY THE VERIFICATION
   RULES TO THE OUTCOME OF THE PROCESSED DATA VERIFICATION
   AND TAKE INTO ACCOUNT THE PREVIOUS RESULTS AND OTHER
   PATIENT INFO. OTHER TYPES (NON-DERIVED)

NOTE: RESULTSETS WHICH REPRESENT "DERIVED" RESULTS
ARE VERIFIED IN THE SAME WAY.

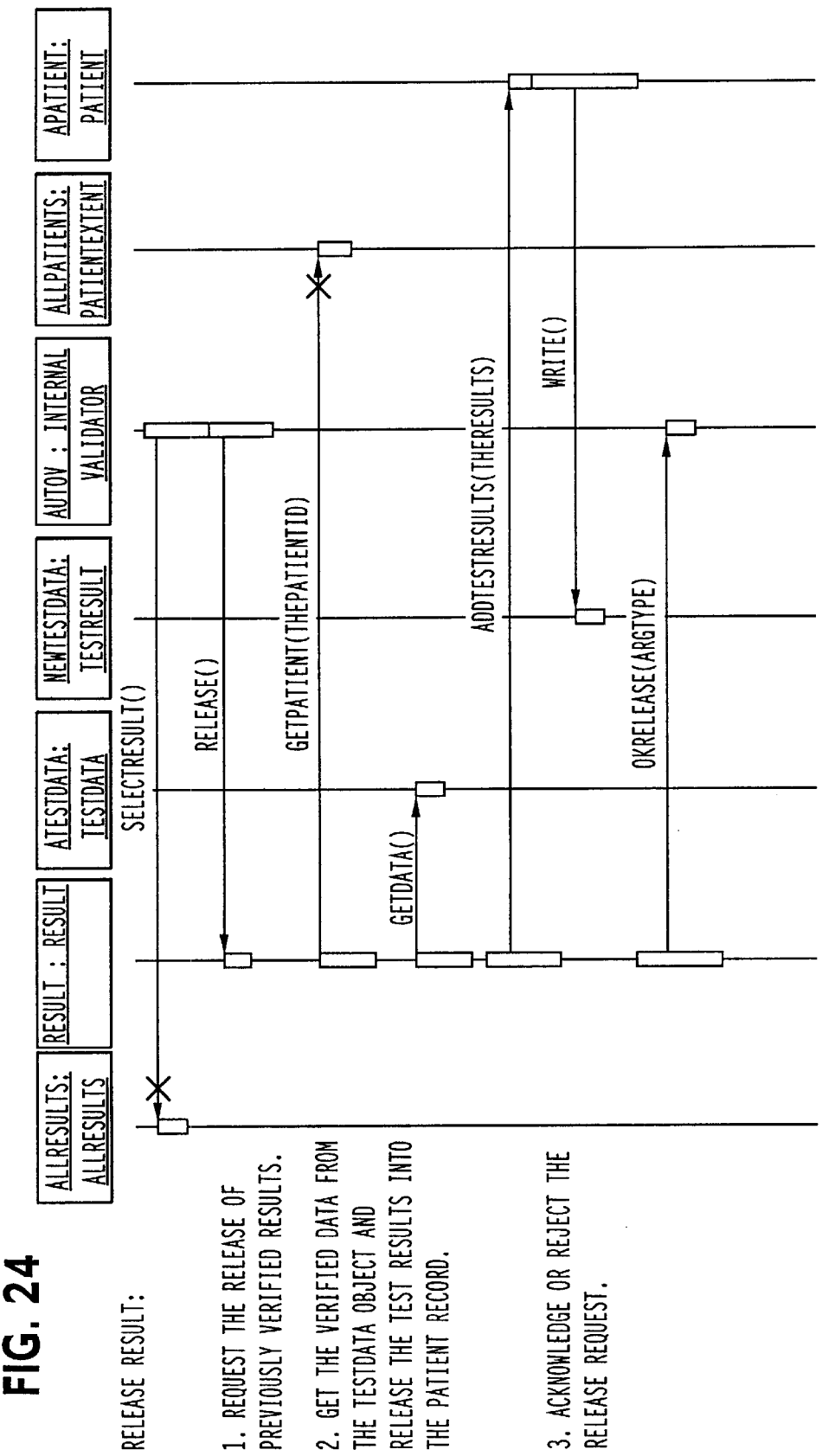

AUTOMATED LABORATORY SOFTWARE ARCHITECTURE

BACKGROUND OF THE INVENTION

1. Technical Field

This invention concerns a software architecture for an integrated clinical laboratory system, and more particularly for automatically performing pre-analytical, analytical and post-analytical processing associated with laboratory testing.

2. Description of the Related Art

Testing of laboratory specimens is an important and integral part of the health care system and hospital operations. The results of such tests are often of critical importance in determining patient care and must therefore be provided reliably and efficiently at all times. However, in contemporary hospitals and independent analytical laboratories, the volume and variety of testing to be performed present a continual challenge to find more reliable and efficient means for managing, carrying out and reporting such tests.

Cost is also a factor which must be considered in the present health care environment. Hospitals and clinical labs are under increasing pressure to provide more and better results with less money. Accordingly, in order to survive, they must continue to find new and better ways to provide high quality care and testing at a reasonable price. One important cost factor associated with analytical testing can be attributed to the number of individuals required to maintain, operate and manage a clinical laboratory. Numerous individuals are needed for all manner of activities relating to the pre-analytical process, the analytical process, and the post-analytical process. For example, the pre-analytical process has typically included order entry, specimen collection and labeling, specimen receipt, specimen sorting, aliquoting, specimen delivery, work load balancing, and ordering reflex testing. The analytical process has traditionally included quality control analysis, analyzer checks, specimen identification, sample analysis, sample preparation and test repeats. Finally, the post-analytical process includes test data review, result verification, quality assurance analysis; insurance claims, result data storage, specimen storage, and specimen retrieval.

In order to reduce costs, various automated systems have been developed to assist in one or more of the process steps which are outlined above. However, such systems have typically been limited to processing exclusively associated with either the pre-analytical process, the analytical process, or the post-analytical process. In some cases communication interfaces have been provided to permit systems in one process area to communicate with systems in other process areas. However, such systems nevertheless fail to provide a comprehensive architecture which facilitates a truly integrated framework which is easily scalable in features, functions, and process areas.

For example, U.S. Pat. No. 5,614,415 to Markin discloses a method for automating a portion of the analytical process. In Markin, a doctor can request a test by entering data into a generalized hospital information computer system (HIS). This information is forwarded by the HIS to a separate laboratory information system (LIS). The LIS then assigns a technician to retrieve a specimen and provides a container having an identification code. The identification code can be cataloged at a receiving station. Information regarding the specimen and test to be performed is retrieved from the LIS and is subsequently used to automate various aspects of specimen transport. The system uses the LIS information for routing the specimen by conveyor to workstations where a required test is to be performed, prioritizing specimens for testing, and transmitting test results entered via a keyboard at the workstation to the LIS. The LIS may then communicate with the HIS or to the doctor by a separate workstation.

Another such system is disclosed in U.S. Pat. No. 5,631,844 to Margrey et al. The system includes a plurality of remote analyzing instruments, located for example at outpatient clinics. The plurality of analytical instruments at remote locations each interfaces with a dedicated computer having a local display to activate and interact with the analytical instrument. The computer also serves as an interface between the analytical instrument and a server. The server is for storing databases, including patient demographics and analysis results and for permitting automatic retrieval and storage of data on an interactive basis to a variety of users. A central laboratory with another computer and display interacts with the dedicated computers through the server to review, evaluate and accept or reject specimen analysis.

European Patent No. EP 0 676 053-B1 (WO94/15219) is related to U.S. Pat. No. 5,614,415 and discloses a method for automatically testing and tracking a specimen in a laboratory. The system utilizes a conveyor to move specimens to and from work locations. Each specimen and its carrier are marked with a machine readable code. Information is added to a computer database relative to each specimen, including the information as to the tests to be performed on each specimen, its machine readable code, as well as priority information. The specimens are moved by the conveyor to each work station where tests are performed and data concerning the test results is inputted to the computer database.

A major disadvantage of each of the prior art systems described above is that they fail to provide a comprehensive software architecture solution which is scalable for implementing some or all of the comprehensive collection of tasks associated with laboratory testing. These disadvantages are attributable, at least in part to the conventional view of a clinical laboratory work flow which has evolved over time. In particular, such systems have conventionally separated out processing associated with the pre-analytical, analytical, and post-analytical tasks described above. In compliance with this traditional view, conventional clinical laboratory systems have primarily been designed as independent and/or autonomous systems. This view obstructs the use of new computing technologies and is an obstacle to the total automation of laboratory work flow.

SUMMARY OF THE INVENTION

The invention concerns an integrated clinical laboratory computer software system for testing a specimen. One or more specimen processing modules are advantageously provided for performing particular predetermined tests on the specimen. Integrated work flow automation programming communicates with any of the plurality of specimen processing modules. The specimen processing modules can include instrument hardware and embedded process control software.

The work flow automation programming includes 1) request processing programming for processing a user request for any of the tests which are available to be performed by the specimen processing modules, and also includes 2) functional control programming providing functional control of specimen processing modules for performing any of the tests, and which further includes 3) result data management programming which provides processing of test result data of any of the tests. Integrated user interface programming communicates with the integrated work flow automation programming for permitting a user to control and monitor all aspects of the computer system operation, including pre-analytical, analytical and post-analytical tasks.

According to one aspect of the invention, the work flow automation programming further includes programming for allocating and scheduling a set of test requests as between different ones of the specimen processing modules when a plurality of requests for tests have been received and are in need of processing.

According to another aspect of the invention, at least one specimen delivery module is provided for transporting specimens to and from the specimen processing modules and the work flow automation programming further includes programming for controlling specimen position, routing and distribution to processing sites where each of the specimen processing modules perform the tests. The work flow automation programming can further include programming for evaluating compliance of test procedures with quality control requirements.

One important aspect of the invention is that the work flow automation programming is assembled from a plurality of system user objects, each encapsulating a separate user operational category. The plurality of system user objects advantageously include (1) a test operator object for processing user test requests and providing test operation status information for any of the plurality of specimen processing modules and (2) an instrument operator object responsive to user commands for controlling operational modes and status for any of the specimen processing modules.

According to another aspect of the invention, the system user objects can further include one or more objects, such as (3) a service tech object responsive to user commands for performing service tasks relating to maintenance of any the specimen processing modules, (4) a result verifier object responsive to user commands for manual verification of test result data provided by any of the specimen processing modules, and (5) a system administrator object responsive to user requests for managing configuration of the computer system. Finally, the plurality of system user objects can also include a bar code reader user object responsive to user inputs delivered via bar code reading devices. By providing discrete programming objects directed to each user rather than specific functions, the system achieves a level of integration and scaleability which is substantially improved as compared to the prior art.

According to one embodiment of the invention, the work flow automation programming can include programming for maintaining a database of test result data received from of the specimen processing module. Such test result database is preferably accessible by the programming for result data management described above.

The work flow automation programming can advantageously include programming for verifying medical insurance code data provided for a particular test which has been requested. Such programming can be accessed by either the request processing programming or the result data management programming to facilitate billing for testing which has been performed.

BRIEF DESCRIPTION OF THE DRAWINGS

There are shown in the drawings embodiments which are presently preferred, it being understood, however, that the invention is not limited to the precise arrangements and instrumentalities shown, wherein:

FIG. 14 is an object interaction diagram of the invention illustrating a common fragment of test order processing.

FIGS. 22–25 are object interaction diagrams of the invention illustrating a basic sequence in which test data delivered by specimen processing modules can be processed, verified and released.

DETAILED DESCRIPTION OF THE INVENTION

Figure 1:
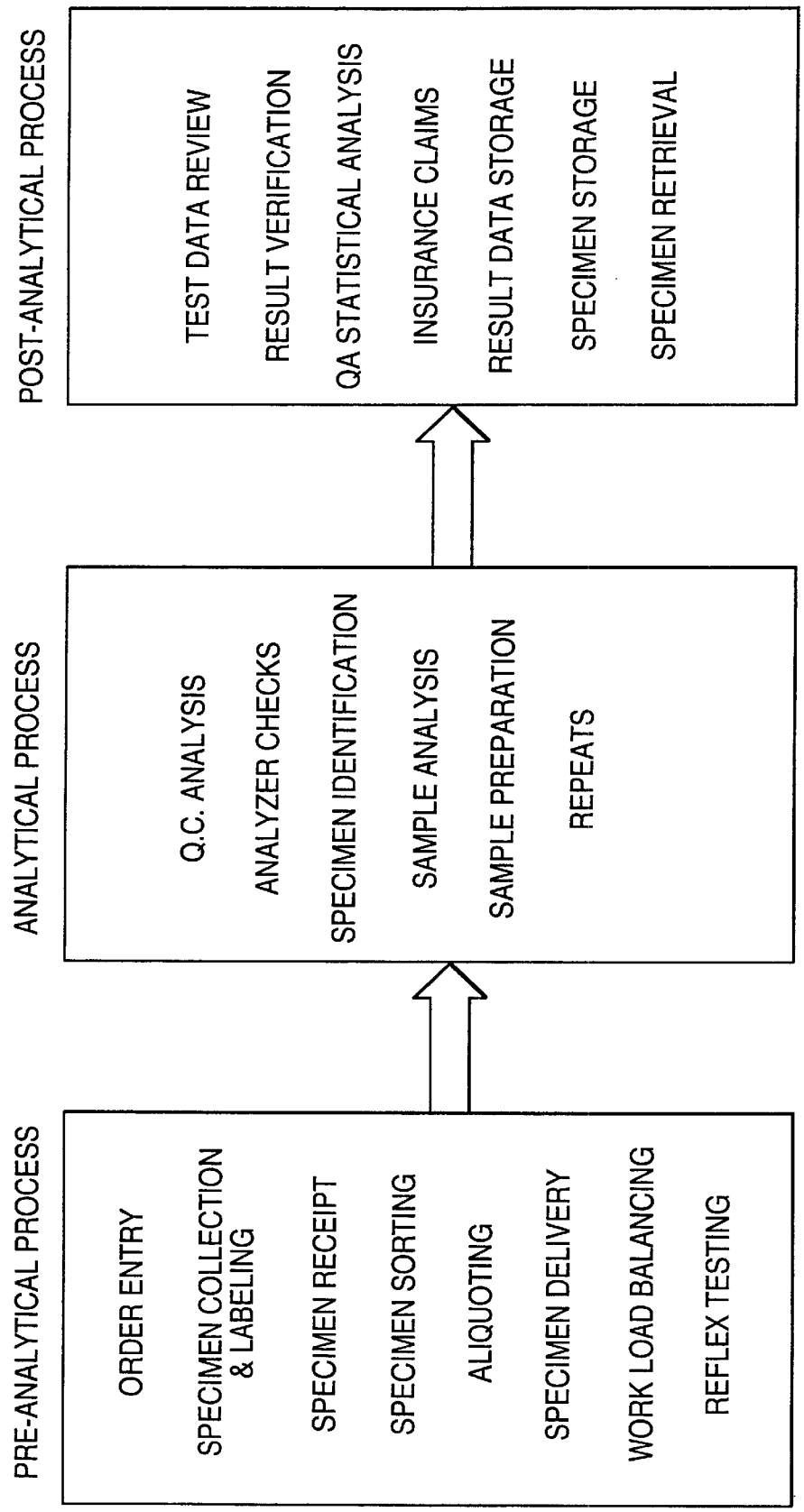
FIG. 1 is a block diagram showing a clinical laboratory work flow process segregated into three distinct phases.

FIG. 1 is a block diagram showing a clinical laboratory work flow process segregated into three distinct phases. This contemporary conceptual view of a clinical laboratory work flow illustrates the pre-analytical, analytical and post-analytical processing operations which have evolved over time in the industry. This conceptual view, with its well established demarcation lines is based on manual operations prevalent in the past. Although useful, the contemporary view has proved to be a conceptual obstacle to applying new computing technologies and the total automation of laboratory work flow.

Figure 2:
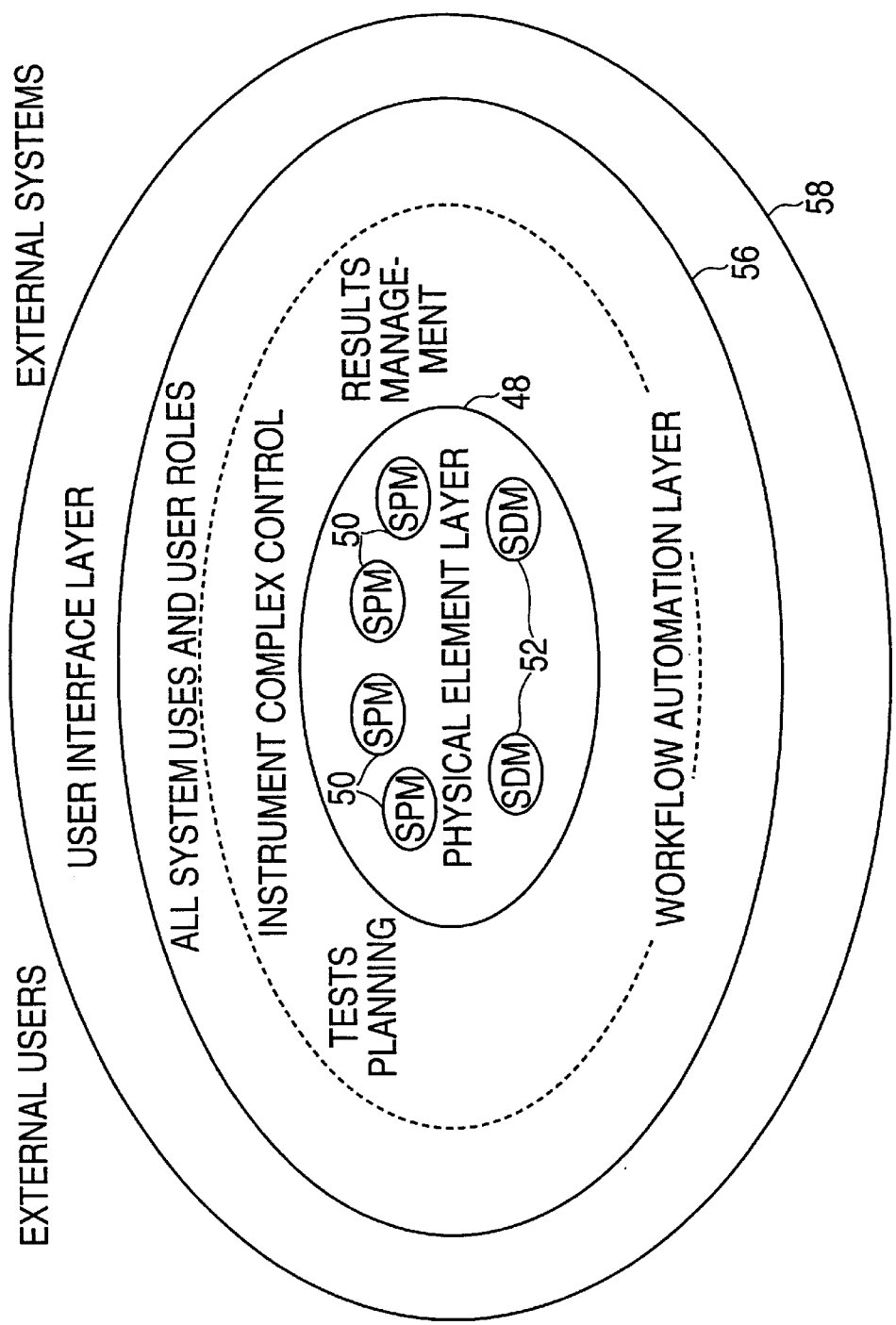
FIG. 2 is a diagram showing the conceptual layers of an automated laboratory computer system of the invention.

FIG. 2 is a diagram showing the conceptual layers of an automated laboratory computer system of the invention which shall be referred to herein as the Virtual Instrumentation Framework Architecture ("VIFA"). The VIFA represents a new solution to the problem of laboratory automation and is based on a radically different conceptual view of the clinical laboratory domain. This conceptual view de-emphasizes differences between Pre-Analytical, Analytical and Post-Analytical processing and focuses, instead, on the laboratory domain as a single Virtual Instrument (VI). The VI conceptual view is captured in form of a model, which allows analysis and decomposition of the domain thus defining VIFA features and design concepts. The VIFA encapsulates all laboratory operations and, even, different laboratory work flows.

As shown in FIG. 2, the invention makes use of an active collaboration of information-processing entities within a distributed software architecture. This framework architecture is also open with respect to any specific implementation of instruments and of specimen transport mechanisms. This presents a new approach that enables building a solution based on single system architecture versus a solution based on custom integration of independently conceived and separately designed systems. A significant advantage of the architecture shown in FIG. 2 is its scaleability (up and down) with regard to various features, functions and test instruments. In this regard, the invention can be viewed as an application domain specific framework which consists of collaborating software entities.

According to a preferred embodiment of the invention shown in FIG. 2, the traditional concept of the test Instrument is eliminated. In its place, the VIFA framework provides a set of specimen processing modules (SPM) 50. Each SPM is a hardware/software entity that is under the control of VIFA workflow automation programming. The SPM is responsible for implementing the programming of processing and/or analyzing the specimen. For example, the SPM can include specimen preparation, specimen testing, or test data delivery. Each SPM 50 preferably encloses all instrument hardware and embedded process control software within a component of the VIFA framework, namely the physical instrument shell.

According to a preferred embodiment, each SPM 50 is completely represented within work flow automation layer by the type of instrument and application capability provided in hardware and its embedded software. Although, as separate elements of the instrument complex, these SPM entities are unaware of each other. Together, the SPM entities represent a population of VIFA's physical element layer.

The system according to the invention may be implemented on any suitable computer operating system which has multi-taking and multi-threading capabilities. For example, the basic system may be implemented using the Windows family of operating systems, such as UNIX, Windows NT or Windows 98 which are available from Microsoft Corporation of Redmond, Wash. However, the system is not limited in this regard, and the invention may also be used with any other type of computer operating system. The system as disclosed herein can be implemented by a programmer, using commercially available development tools for the operating systems described above. Suitable hardware for implementing the system can include computer systems incorporating Pentium II or III brand microprocessors available from Intel Corporation or any similar microprocessor.

The various layers comprising the conceptual system architecture are shown in FIG. 2. User interface layer 58 preferably consists of graphical user interface (GUI) interfaces of lab local and remote workstations and terminals. Under this architecture, external devices used for purposes of entering information into the system, and, specifically, any specimen identification device, such as a bar code reading device, are preferably also elements of user interface layer 58.

A work flow automation layer 56 is provided below the user interface layer 58. The work flow automation layer 56 encompasses and implements complete test request processing, result data management, workload management and multiple instrument control. It also includes functional control over operations of specific instruments, their status monitoring and quality control, distribution of specimens to processing sites, and monitoring specimen positions during the entire process.

The physical element layer 48 is provided below the work flow automation layer 56. The physical element layer preferably includes software used by individual functional hardware elements of the instrument complex. In particular, the instrument complex preferably includes the software modules for SPM's 50, as previously described, and for specimen delivery modules (SDM) 52 used for transporting specimens to and from each test location. The corresponding SPM and SDM hardware elements of the system are preferably made plug compatible within the architecture by this software layer. The SDM can co-exist with manual transportation. More specifically, the system permits and supports manual transportation of the specimen to the SPM which is under the functional control of the work flow automation programming.

Figure 3:
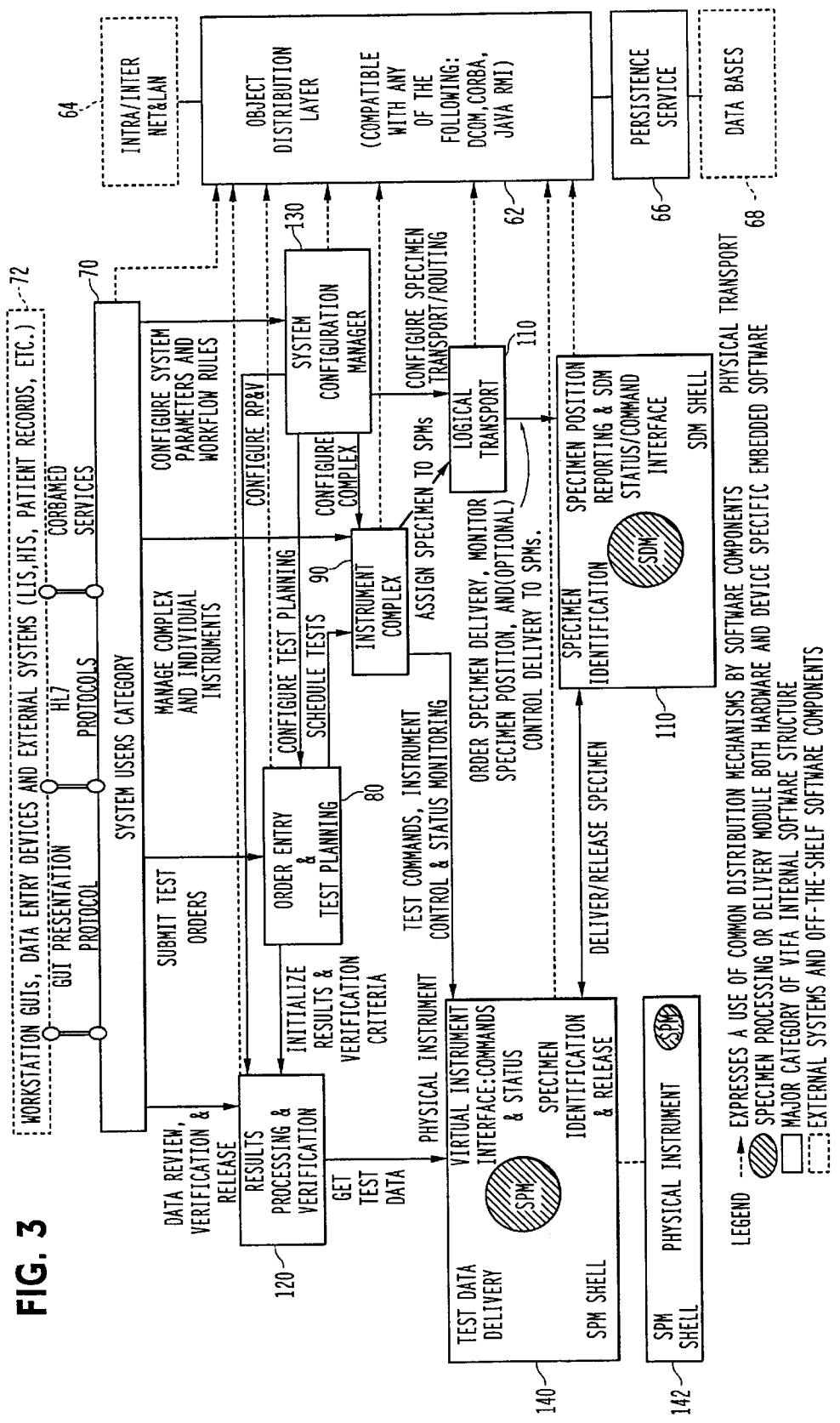
FIG. 3 is a block diagram showing a top level architecture for the automated laboratory computer system of the invention.

FIG. 3, is a block diagram showing a preferred architecture of work flow automation layer 56 and physical element layer 48, which will now be described in greater detail. Each block represents a category of application software objects as identified by each respective block. For the purpose of consistency, those components comprising the work flow automation layer 56 will be described separately from those comprising the physical element layer 48.

Work flow automation layer 56 includes several major blocks or categories, including common infrastructure block 60, system configuration manager 130, system users block 70, order entry and test planning block 80, instrument complex block 90, logical transport block 100, and results processing and validation block 120. Common infrastructure block 60 is the software technology specific layer which isolates the implementation of technology specific software mechanisms. The features of the work flow automation layer 56 are built on top of the common infrastructure block 60. The common infrastructure block 60 implements a variety of infrastructure functions using standard information technology (IT) elements. As shown in FIG. 3, these functions can be provided by object distribution layer 62 for providing object distribution for messaging and exceptions handling, a persistence service block 66 for object persistence, intra/inter-net and LAN block 64, networking, database block 68 for database services, and so on. Those skilled in the art will readily appreciate that most of these technology features can be, optionally, purchased as "off-the-shelf" components and plugged into the common infrastructure layer to provide the required services. Configuration manager block 130 maintains work flow specialization information and manages system configuration.

System users block 70 specifies and encapsulates each system user concept, and isolates the system design issues from concerns with the user interface "look and feel". The internal structure of the system user block reflects different usage specialization with focus on typical application tasks performed by particular types of real system users. As shown in FIG. 3, the system users block 70 communicates with block 72 which includes workstation GUI's, data entry devices, and links to any external computer systems such as laboratory information systems, hospital information systems, and patient record databases.

Specialized roles that are defined within the system users block include the 1) "Test Operator", responsible for tests submission and monitoring, 2) "Instrument Operator", responsible for dealing with instrument operational modes and status, 3) "Service Tech", performs service tasks, either locally or remotely, 4) "Result Verifier", performs operations associated with manual verification of results, 5) "Auto Verifier", automates a function of results verification, 6) "System Administrator", manages system configuration, 7) "BCR User", manages system inputs delivered via bar code reading devices 8) "Peer Laboratory Information System", manages interactions between VIFA based systems and any laboratory information system over a standard bi-directional LIS interface. Additional specialization of the system user concept within the internal structure of the system user block 70 allows bringing new users into the system. It will be readily appreciated by those skilled in the art that any particular type user can be added to the system user block 70 within the VIFA architecture.

Figure 3A:
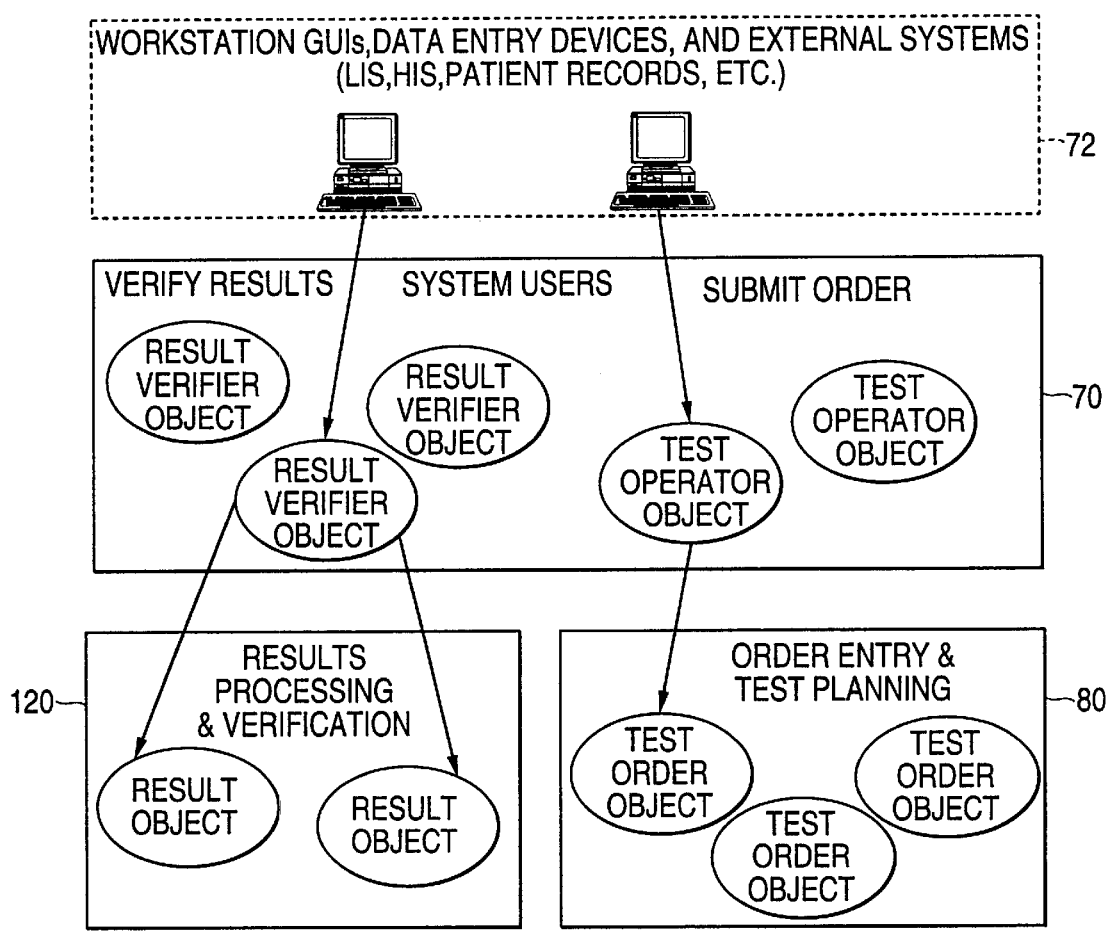
FIG. 3A is a more detailed block diagram showing a portion of FIG. 3.

The objects in the system users block 70 serve as the interface between external entities block 72 (e.g., GUI workstations, laboratory information systems) and the rest of the system. The system users block isolates the concerns and details of data presentation and format (e.g., look and feel) from the rest of the system. FIG. 3A shows an example of an expanded view of a portion of FIG. 3. In this example, one user verifies results, while another user submits a test order. Both end users in the example interact with the system through GUI workstations in block 72. The GUI software interacts with the rest of the system through one or more objects in the system users block 70. The software that handles a results verification screen directs a result verifier object to verify some results. The result verifier object, in turn, interacts with the result objects in the results processing & validation block 120 to change their states to be verified. The software that handles a test order submission screen directs a test operator object to submit a test order. The test operator object, in turn, interacts with a test order object in the order entry and test planning block 80. This example illustrates how the system users block 70 isolates the user and external interfaces in block 72 from the other blocks in the system. For example, the results processing & validation block 120 is unaware of the results verification GUI software and vice-versa.

Referring again to FIG. 3, it can be seen that the system user block 70 communicates with order entry and test planning block 80. The order entry and test planning block plays a critical role in addressing the work flow management requirements of the system. Order entry and test planning block 80 permits any test to be specified by a user and to be accepted into the processing, provided that the required testing capability is configured in the instrument complex block 90. Multiple and simultaneous test orders from independent entry points are preferably supported within block 80. Further, the order entry and test planning block 80 preferably permits users to combine different test requests into a single work order. Order entry and test planning block 80 is advantageously configured to permit ordering of tests, as well as planning and monitoring of their execution. The order entry and test planning block 80 implements ordering procedures that employ random, discrete, reflex, and repeat testing.

As illustrated in FIG. 3, order entry and test planning block 80 communicates with Instrument complex block 90. Instrument complex block 90 provides complete management functions for any of the different types of SPMs 50 which are supported by the work flow automation layer 56. According to a preferred embodiment, these management functions include but are not limited to, instruments status monitoring and control, test repertoire specification, instrument calibration, and remote diagnostics. The programming contained in the instrument complex 90 is not limited to the foregoing specific functions and it should be understood that the instrument complex can also preferably support any other services required for operating and maintaining SPMs 50 within the complex. Such functions can include workload distribution and on-line configuration management (e.g. addition and removal of instruments). In general, instrument complex 90 implements a layer of abstraction for various types of physical instruments that isolates users of the virtual instrument complex from the physical instrument detail and manages each individual SPM 50 as a resource within the virtual instrument complex.

Instrument complex block 90 communicates with logical transport block 100 as shown in FIG. 3. Logical transport block 100 is configured to enable an integration of various specimen delivery modules (SDMs) 52 which are used for physically transporting specimens within the instrument complex. The logical transport block 100 handles each specimen as a transportable entity, and each SPM 50 as a specimen-processing site with a specified location on a physical transport system. Logical transport block 100 also preferably provides suitable programming to monitor specimen tube location on the transport system and to support specimen routing to a selected SPM 50.

According to a preferred embodiment, the system can handle responsibility for load distribution in generic laboratory work flow in two different ways as between VIFA components 90, 100 and the SDM physical transport resident control in physical transport block 110. According to one embodiment, when a VIFA compatible SDM 52 is used to deliver specimens, then the logical instrument complex block 90 will preferably have total responsibility for the load distribution. Under these circumstances the logical transport block 100 determines specimen destinations and monitors specimen positions. However, in the case of integration with a foreign laboratory automation system which is not VIFA compatible, the participation of blocks 90, 100 in the system load distribution can be, if so desired, reduced to the monitoring of specimen delivery only.

Results processing and verification block 120 communicates with physical instrument block 140 and is responsible for processing and verifying results using portable algorithm services. Block 120 preferably includes suitable programming to support user configurable test criteria, result verification rules, and laboratory specific procedures. Integration of result verification with knowledge based expert systems is also enabled within this component. While the main purpose of the result processing and verification block 120 is to handle the raw data processing and verification semantics of test result data, it also preferably plays a key role in supporting efficient automation of lab work flow. Referring again to FIG. 3, order entry and test planning block 80 communicates with results processing and verification block 120. Thus, results processing and verification block 120 participates in the external integration of the work flow by enabling concurrent use of result verification functions for data accumulated in the system. It also supports the internal integration of automated work flow process by means of collaboration with the order entry and test planning block 80.

With the architecture shown in FIG. 3, other software components can easily be integrated within the system. These software components can include report generators, an information logging facility, data base products, insurance codes verification software, quality assurance statistical packages, ASTM and HL7 protocols, MPI based patient record access, and so called expert systems (to assist in auto-verification of results). Such features can be integrated within work flow automation layer 56 or purchased as "off-the-shelf" components."

With continuing reference to FIG. 3, the components comprising the physical element layer 48 will now be described. Physical element layer 48 includes physical instrument block 140 and instrument specific embedded control software in block 142. Physical element layer 48 also includes the physical transport block 110 which likewise includes physical transport shell provided by a software interface for each SDM 52.

Physical instrument block 140 represents different types and/or designs of SPM. The block advantageously offers SPM services via a common application interface. These services are implemented as two distinct modules, namely the physical instrument shell and instrument specific embedded control 142. Physical instrument shell 140 represents an SPM operating environment, which is comprised of policies that are common across different instrument types. The shell specifications represent an external interface of the VIFA that is published to enable integration of independently developed SPMs as a component within the VIFA based system. This commonality enables the work flow automation layer 56 to integrate different SPMs. The integrated SPMs operate under the control of the work flow automation layer 56. In a preferred embodiment, the common infrastructure 60, which is used in the work flow automation layer 56, can be also used to facilitate construction of the physical instrument shell 140.

The common policies implemented in the physical instrument shell 140 preferably include 1) specimen identification and reporting the specimen identification to the work flow automation layer 56, 2) result data generation and delivery to work flow automation layer 56, 3) processing of control commands, 4) processing of specimen analysis commands, 5) instrument status reporting and 6) instrument maintenance support (i.e. diagnostics). Specimen identification can be accomplished using any of several techniques, such as bar coding or other machine readable markings, which are well know in the art. Alternatively, the specimen identification and reporting the specimen identification can be provided in the SDM or SPM shells.

The instrument specific embedded control software 142 is responsible for process control and real-time data acquisition. This software is designed to meet specific requirements of process control and real time data acquisition of any instrument hardware design, and it may or may not be common between different SPM types.

In FIG. 3, the physical element layer 48 also includes physical transport block 110, which controls the hardware for one or more SDMs. The operations of the SDMs are monitored and controlled by the logical transport block 100. According to a preferred embodiment, the basic structure of the physical transport category is similar to the structure of physical instrument category.

The architecture described above relative to FIG. 3 represents a unique division of responsibilities within the distributed software system and presents the structural aspect of the VIFA according to a preferred embodiment of the invention. The framework is open to extensions through the published interfaces of the work flow automation layer 56.

The above-described blocks in FIG. 3 each encapsulate a category or sub-category of software objects comprising the VIFA according to a preferred embodiment of the invention. These objects play a key role in ensuring that the various components of VIFA are able to interact in a coordinated and synchronized manner. These interactions achieve complete control of laboratory work flow operations on an arbitrary instrument complex. In addition, when adapted as extension points of the VIFA framework, these objects facilitate the specialization of the framework. The interaction of the various objects is represented in FIGS. 4–12, and 26 in Unified Modeling Language (UML) notation. Additional information on the objects and their methods is provided in FIGS. 13 to 25.

The description discussed below focuses only on a minimal set of features and interfaces required for constructing a generic instrument system according to a preferred embodiment of the invention. However, it will be readily appreciated by those skilled in the art that the foregoing objects or constructs can be implemented to provide a variety of additional features as may be required in the laboratory environment, and the invention is not intended to be limited in this regard. Prior to considering the object representation in FIGS. 4–12 and 26 and the corresponding methods in FIGS. 13–25, a brief description of each of the principal software objects is appropriate.

As shown in FIGS. 4–12, the key objects according to a preferred embodiment can include: a logical instrument object 202, test activity object 204, test plan object 206, specimen object 208, test data object 210, test order object 212, result object 214, result set object 216, load distributor object 218, instrument collection object 220, tracking point object 222, transporter object 224, and system user object 226. Each of these important objects will now be described.

The logical instrument object 202 is an object within the instruments complex block 90 representing a single SPM entity within the work flow automation layer. This object captures characteristics of an SPM 50 as an operational component. When integrating a new type of SPM 50, the logical instrument object 202 may be specialized in terms of its commands and responses. Nevertheless, the logical instrument object's behavior within the work flow automation layer remains unchanged.

The test plan object 206 describes a specimen in terms of the test activities it is subjected to. It also provides dynamic representation of the state of all tests ordered on a given specimen. The test plan object 206 is uniquely associated with a corresponding specimen object 208 as shall hereinafter be described Test activity object 204 represents a single activity within the context of specimen processing. Each test activity object 204 is an atomic unit of work and point of coordination of the operations performed by the categories of the work flow automation layer 56. Test activity objects 204 are created within instrument complex block 90 by the test plans object. A logical instrument object 202 maps a test activity object 204 into a specific command from an SPM supported repertoire. The mapping of a test activity object 204 into commands is determined by the SPM embedded process implementation. According to a preferred embodiment, the test activity object 204 is not required to change to support a new SPM. Instead, a new mapping of test activity objects 204 into commands for the new SPM is defined. This mapping facilitates the extension of the logical instruments complex 90.

The specimen object 208 identifies a specimen as a transportable material and describes a specimen in terms of its physical characteristics (for example, container type and current volume) and its location (for example, en-route to lab, position within the instrument complex, in-storage, etc.). Each specimen object 208 is uniquely associated with a corresponding test plan object 206.

The test data object 210 is another extension point of the instrument complex 90. The test data object 210 is a composite object and its structure can be specialized to match any data produced by an analytical SPM. New specializations of test data objects 210 can be expected when defining a new SPM.

Test order object 212 is a requisition for work to be performed on one or more specimens. Test order object 212 creates one or more test plan objects 206 which in turn create one or more test activity objects 204. This enables implementation of both, simple orders, which are restricted to test orders on a single specimen, and complex orders, which combine various tests on a set of specimens according to arbitrarily specified rules.

Result object 214 contains all data associated with a single test activity object 204 and provides software for managing and processing this data. The result object is specialized by defining algorithms for processing the data.

Result set object 216 represents aggregations of result objects 214 and derivations from result objects. The result set objects 216 enable the grouping of related result objects 214. It also enables aggregation of additional information by combining and processing data from different result set objects 216.

Load distributor object 218 automates the distribution of tests represented by test activity objects 204 within the instrument complex. It also represents an extension point of the framework. Different implementations of workload distribution policy can be provided to accommodate for different system requirements and for different specimen delivery systems.

Instrument collection object 220 is an aggregate representation of all instruments in the instrument complex. It is responsible for monitoring the state of the instruments, maintaining testing capabilities of the complex, and managing addition and removal of an instrument.

Tracking point object 222 represents a location on the specimen transport system that can be used to monitor specimen positions. This location must have hardware in order to associate a specimen with the carrier. For example, barcode reader devices can read labels on a rack and on a specimen tube. Thus the information is delivered via tracking point object 222 associated with the location of the barcode reader device.

Transporter object 224 is responsible for managing specimen delivery to SPMs 50. It contains the routing table between the locations represented by all tracking point objects in the system. The transporter object 224 configures and monitors tracking point objects as different types of destinations. Some destinations can be locations of SPMs 50. Other destinations can serve as entry or exit points of the specimen transport system. In a preferred embodiment, the transporter object 224 can also configure some of destinations to serve in more than one role. As the key enabler of integration of the laboratory automation system function, the transporter object 224 also represents an important extension point of VIFA.

System user object 226 represents a basic type of user in the VIFA based system according to the invention. This object is specialized to support user interactions with the automated system, as required for a particular type user's participation in the system activities. System activities preferably performed by this object include test ordering activities, test results monitoring, review and verification activities, quality assurance activities, activities associated with configuring the system, instruments maintenance and service activities, and so on.

FIGS. 4–12 demonstrate the novelty of the VIFA structure and the integration of at least two, preferably three, and most preferably four elements of laboratory work flow within a single architecture. These four major elements comprise: 1) information flow management, 2) material flow management, 3) instruments management and 4) specimen delivery management. Specifically, these figures describe class structures that are capable of providing support for the following major operations: 1) orders processing and workload distribution, 2)managing and tracking delivery of specimens to SPMs, 3) coordinating analytical processing on multiple SPMs, 4) specimen processing at SPMs, 5) consolidating test data from multiple SPMs, 6) consolidating review and release of results from any set of instruments, 7) maintenance of SPMs within the instrument complex, such as individual SPM calibration, and 8) consolidated processing of instrument status information from multiple SPMs.

Figure 4:
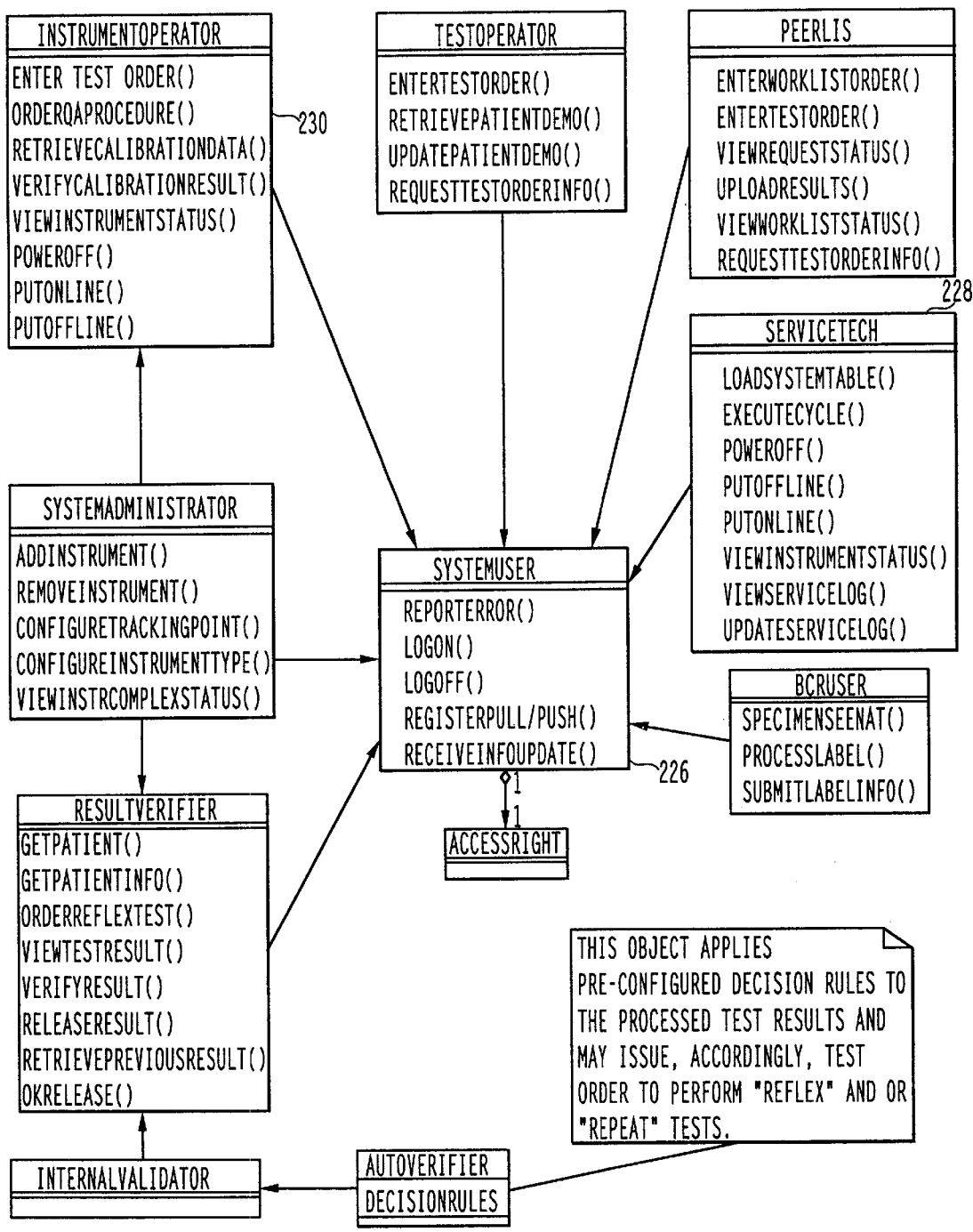
FIG. 4 is a class diagram showing the system users category structure of the invention.

FIG. 4 demonstrates the structure of system user objects 226 that have been previously described. This structure shows a representative set of objects and sample interfaces applicable in a system comprised of hematology instruments. Adding another type of instrument, such as a chemistry analyzing instrument, would require extending the class structure shown in this diagram. For example, to include support for a chemistry instrument, new methods can be added to the service tech 228 and instrument operator 230 object classes.

Figure 5:
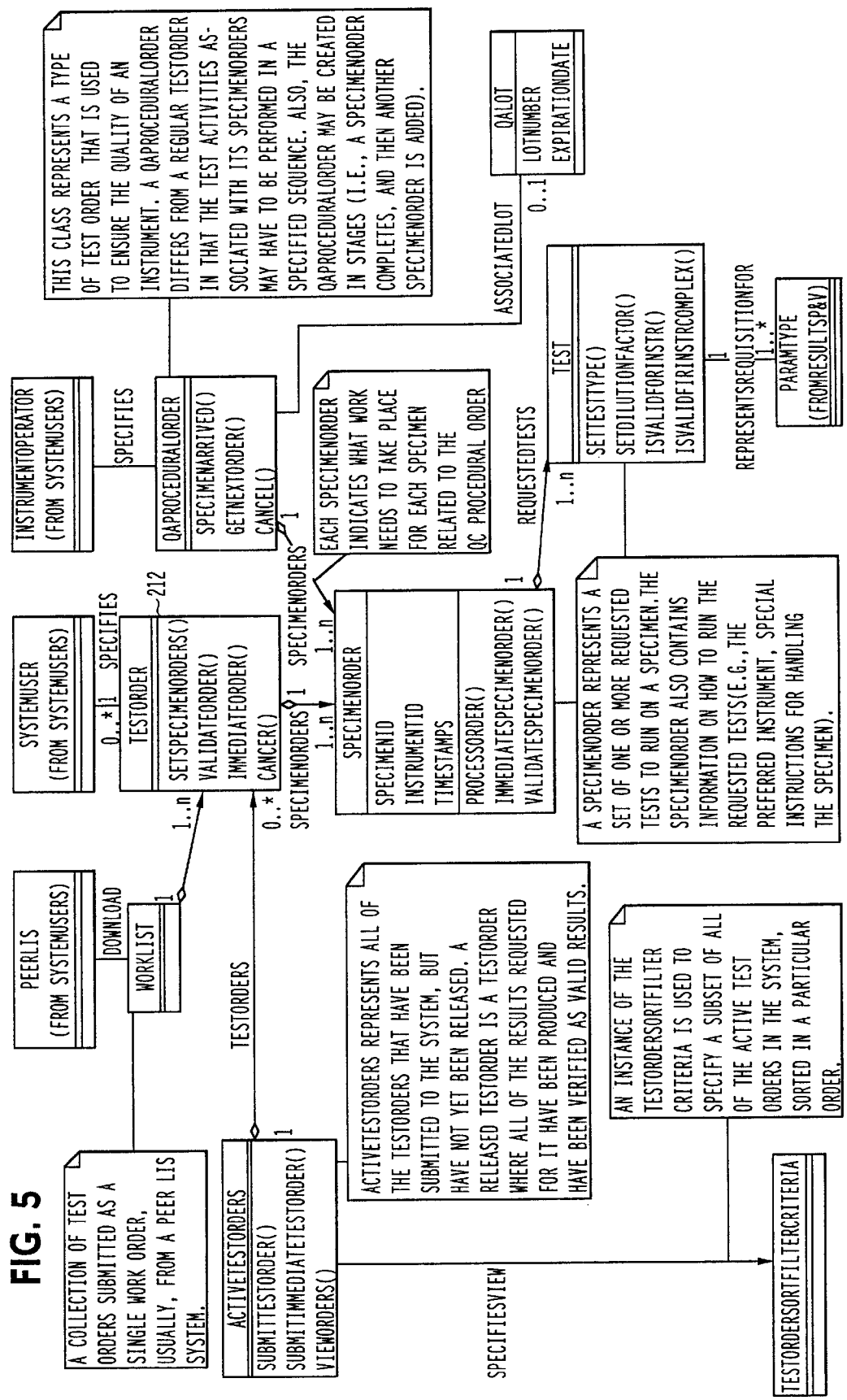
FIG. 5 is class diagram showing the test planning category—work orders sub-category structure of the invention.
Figure 6:
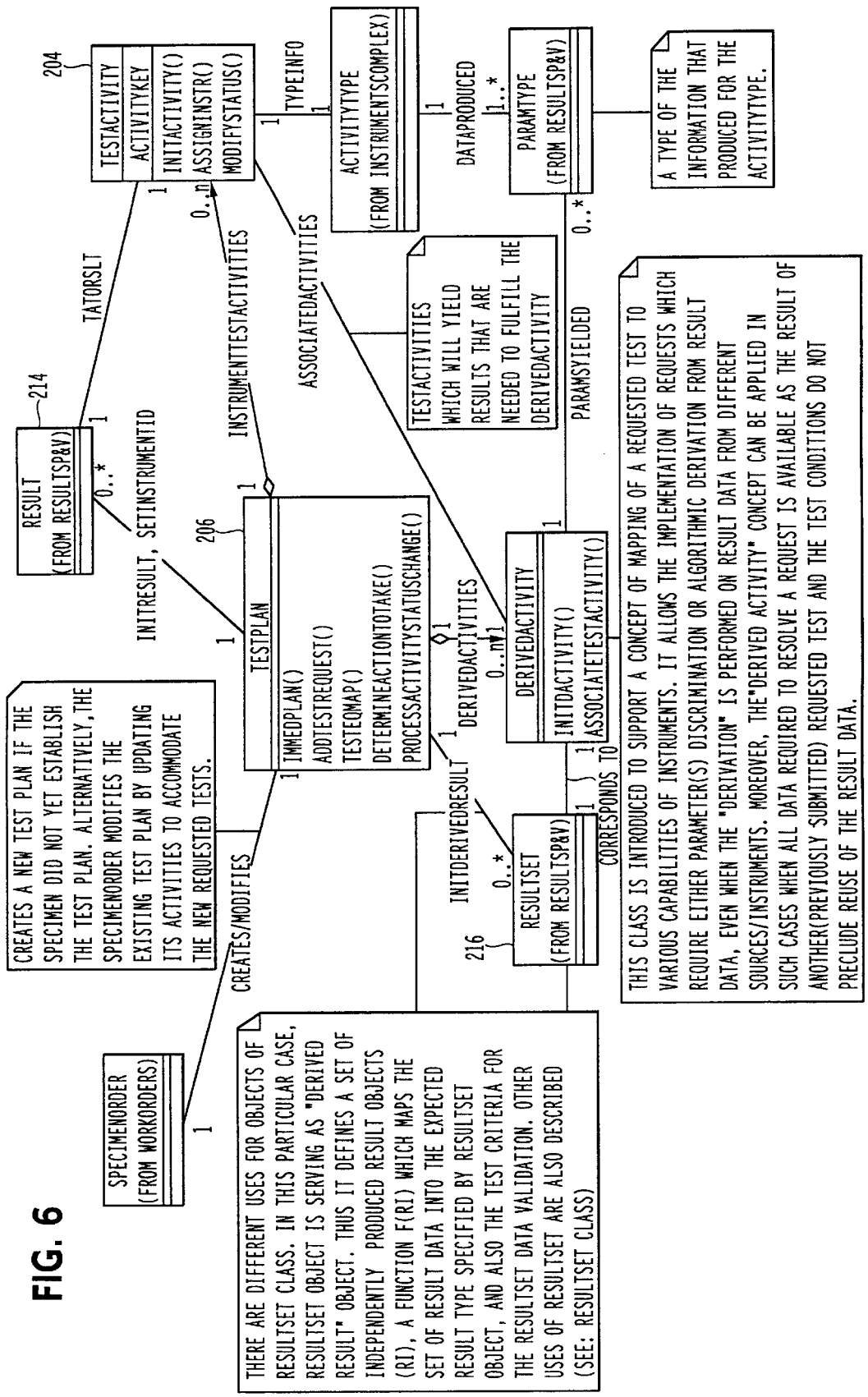
FIG. 6 is class diagram showing the test planning category—test plans subcategory/results relationships structure of the invention.
Figure 7:
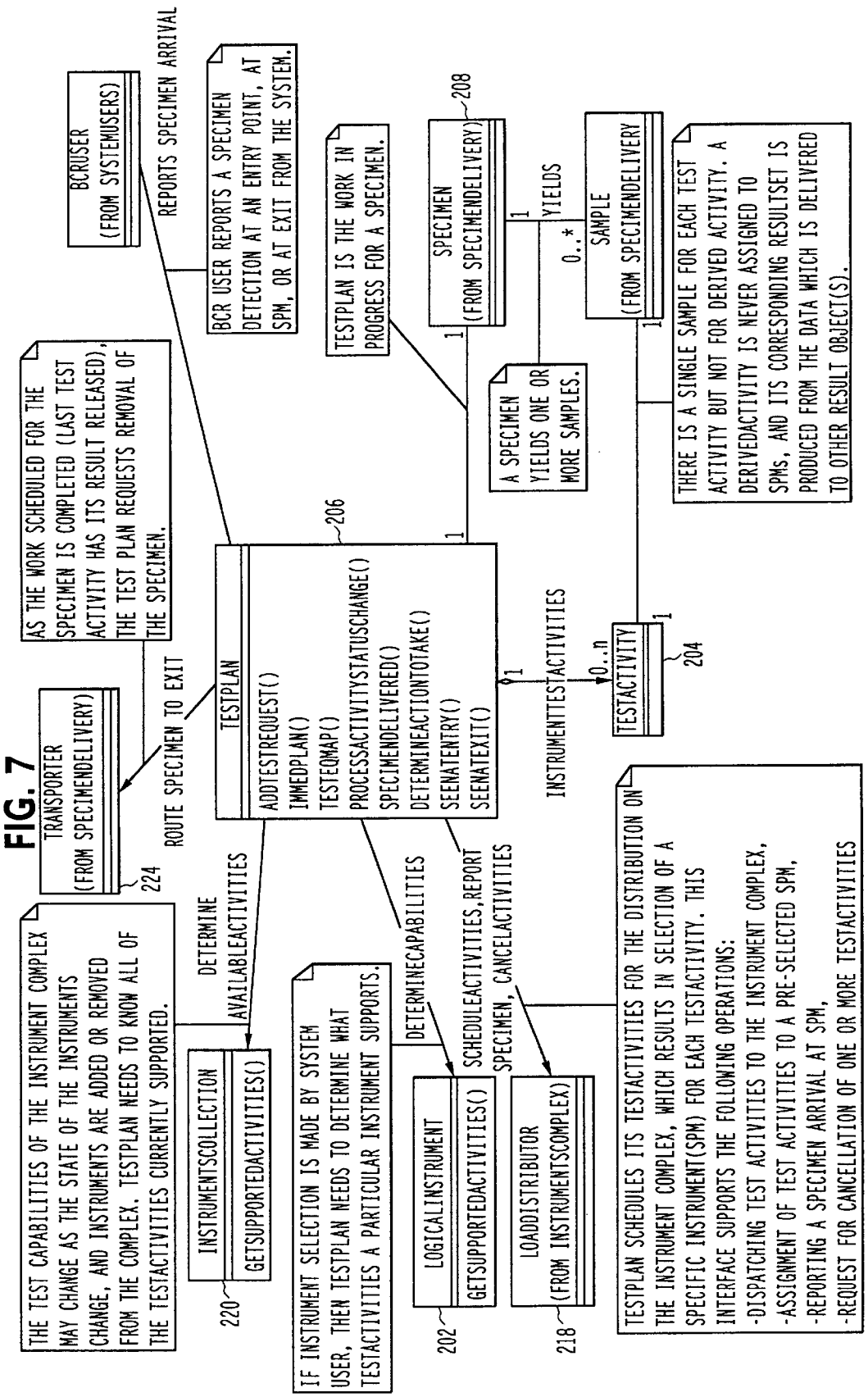
FIG. 7 is class diagram showing the test planning category—test plans subcategory structure/relationship to instruments and transporter of the invention.

FIGS. 5, 6 and 7 further describe the internal structure of the order entry and test planning block 80. Test planning block 80 is comprised of two distinct subcategories objects, namely test orders and test plans. Objects in the test orders subcategory support an ability of external users to specify tests and to monitor associated test orders. Within the test orders subcategory, the test order object 212 represents a request to perform a set of one or more related tests. The objects of the test order subcategory are responsible for processing and monitoring all test orders. The methods of the objects of this subcategory allow the system to: 1) identify and interpret user test orders coming from various system interfaces, 2) create internal test order objects 212 and communicate the test request information to test plan objects 206 within the test plans subcategory, 3) monitor specified activities updated by other categories to manage state of test order objects 212 and to support an interface with a system user, (for example, test order status to a submitter of the test order), 4) cancel a test order, as required, 5) delete test order objects 212 when tests are completed or canceled.

The test plans subcategory of block 80 is responsible for managing of test plan objects 206, while processing and monitoring test activity objects 204 for all specimens in the system, in the following general order: 1) create test plan object 206, 2) create test activity object 204 for work requisitioned for a test plan, 3) initialize result object(s) 214 that correspond to test activity objects 204, 4) dispatch test activity object(s) 204 to load distribution object 218 contained in the instrument complex block 90, 5) manage the state of test activity object 204 and test plan object 206 by monitoring specified activities updated by other categories, 6) cancellation of test activity object 204, as required, and 7) deletion of test activity object 204 and test plan object 206 when specimen processing is completed. The class diagrams in FIGS. 6 and 7 demonstrate relationships between objects 206 of the test plan subcategory and objects of other categories that facilitate steps from (1) to (7) above.

FIG. 6 highlights relationships between objects 206 of the test plans subcategory in block 80 and objects of result processing and verification category of block 120 that are instrumental in steps (1) to (3). FIG. 7 shows structural relationships between test plan object 206 and objects from instrument complex category of block 90, logical transport category of block 100 and system users category of block 70. These relationships are used for implementing steps (3) to (5) which in turn provide support for distribution of activities within the instrument complex block 90 and for specimen tracking and delivery within the logical transport block 100.

Figure 8:
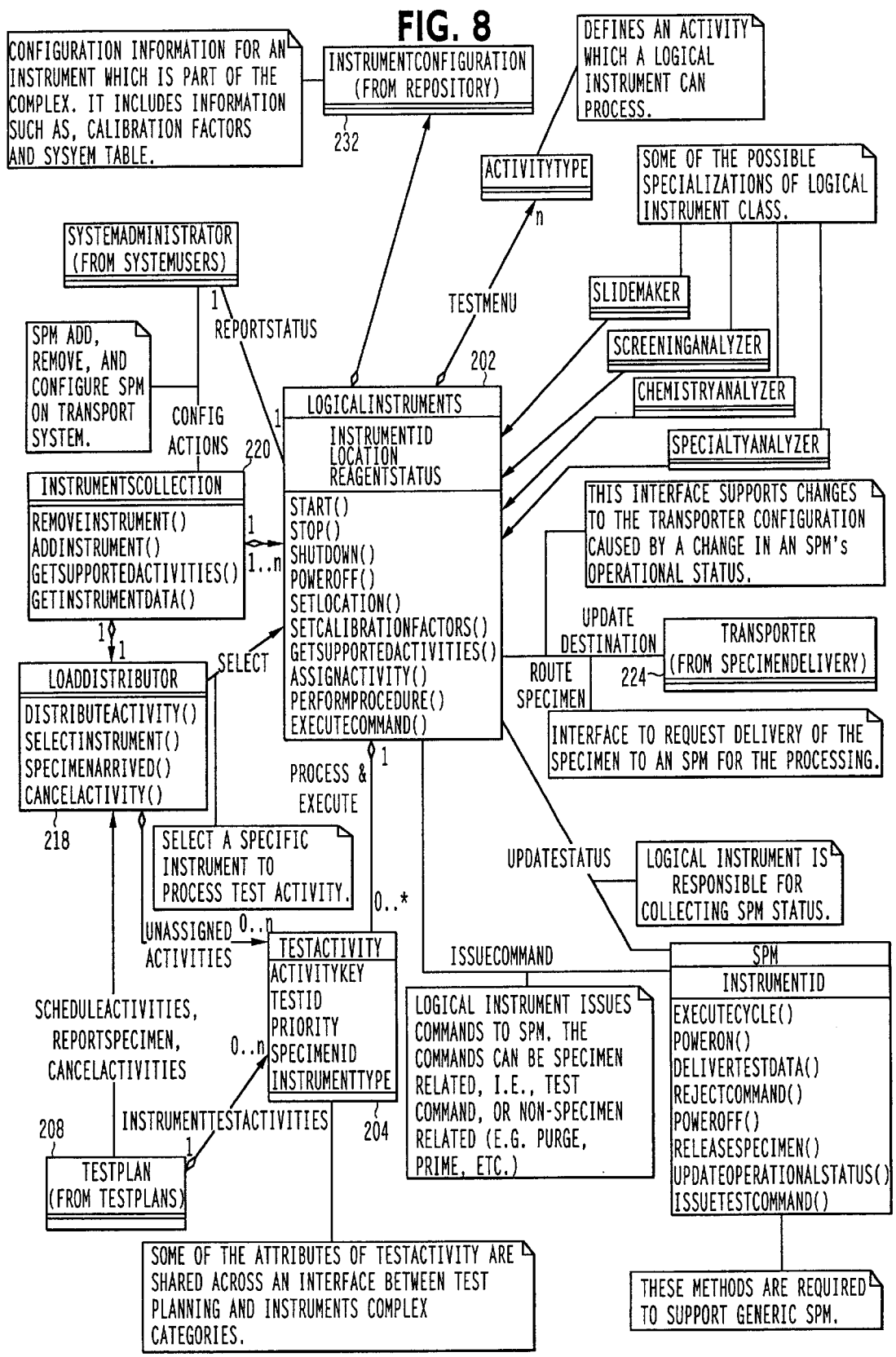
FIG. 8 is class diagram showing the instrument complex category structure of the invention.

The objects that allow the instrument complex category of block 90 to consolidate control over instruments (SPMs) and to facilitate processing of specimen on SPMs are shown in FIG. 8. The following steps performed in this category contribute to processing tests on an instrument complex: 1) processing test activity objects 204 dispatched from the test plans subcategory of block 80, 2) selecting SPMs and assigning test activity objects 204 to the logical instrument objects 202 which represent the selected SPMs, 3) issuing commands to SPMs and submitting requests for specimen delivery to logical transport category, and 4) monitoring the state of assigned test activity objects 204.

Also, contained in the instrument complex category of block 90 are the major common steps of managing an individual SPM within the instrument complex. These are as follows: 1) adding SPMs to the instrument complex (creating logical instrument object 202), 2) putting SPMs on-line, 3) monitoring and reporting SPM status, 4) putting SPM's off-line, and 5) removing SPMs from the instrument complex (deleting logical instrument objects 202). The structure and interface of instrument collection object 220, load distributor object 218, logical instrument object 202, and instrument configuration object 232 provide the information and methods that are used for implementing the above two sets of operations.

Figure 9:
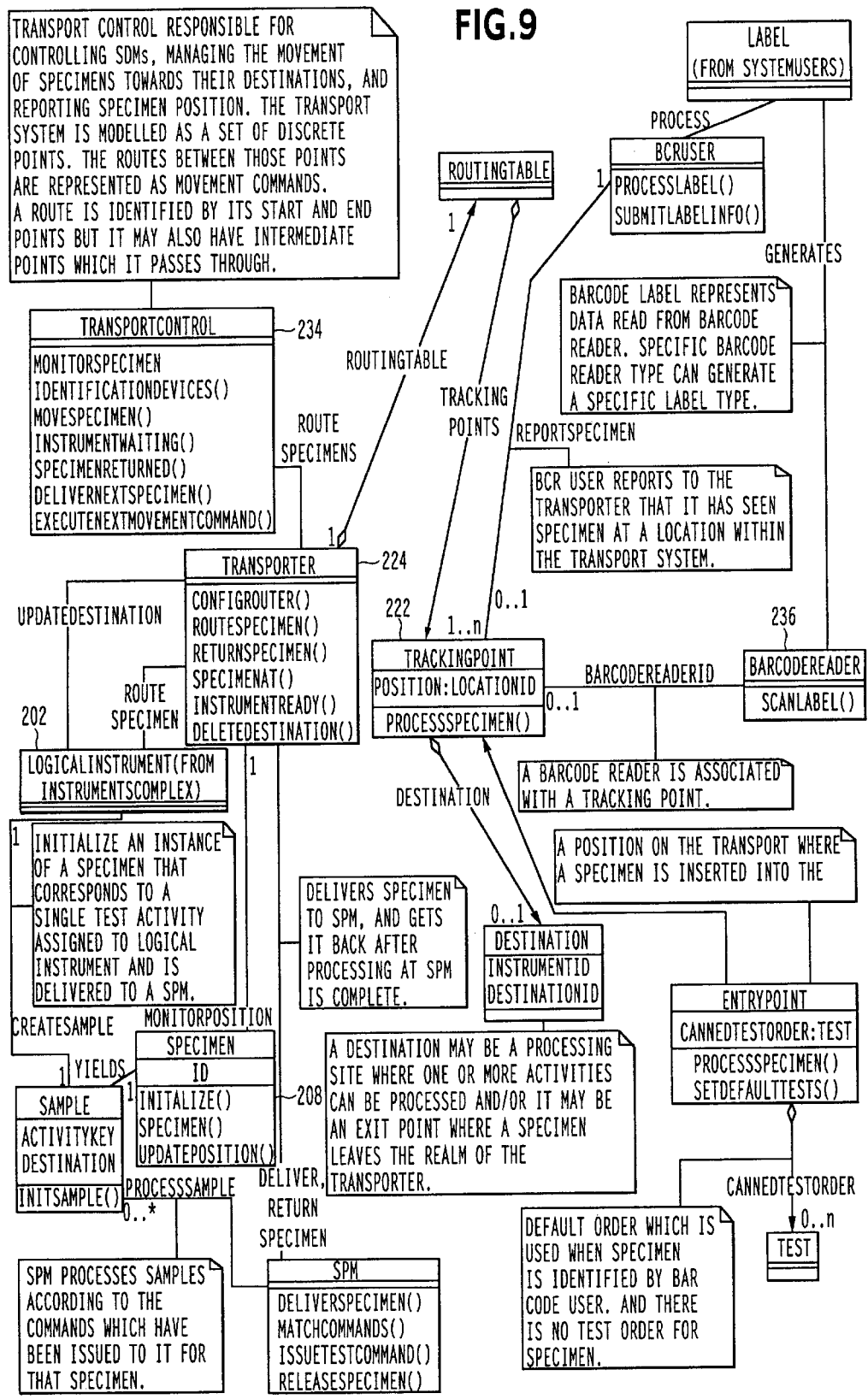
FIG. 9 is a class diagram showing the logical transport category structure of the invention.

The class diagram in FIG. 9 illustrates the structure of the logical transport category of block 100. This category enables integration of the specimen transport element of work flow within VIFA. The logical transport category of block 100 emphasizes monitoring of specimens within the system and managing the delivery of those specimens to the intended destinations. These functions are supported within the logical transport category by the following steps: 1) processing specimens entry (creating specimen objects 208), 2) processing specimen delivery requests from logical instrument objects 202, 3) issuing commands to the transport system controller 234, 4) tracking specimen positions by collecting reports from specimen identification devices such as bar code reader 236, 5) managing status of specimen objects 208 (e.g. volume, position, etc.), and 6) processing specimen exit (deleting specimen objects 208).

Also, there are other operational steps performed within the logical transport category supporting a general task of managing the instrument complex configuration. These steps are related to the common steps of maintaining an individual SPM that are described above and include: 1) configuring specimen identification devices, such as a bar code readers, on the transport system (creating tracking point objects 222 and associating the position of the specimen identification device with a location on the transport system), 2) configuring SPMs on transport system (associating SPMs with tracking point objects 222), 3) removing SPMs from the transport system (disassociating SPMs from the tracking point object 222), 4) removing specimen identification devices, such as bar code readers, from the transport system (removing tracking point objects 222 from the transporter object 224).

Figure 10:
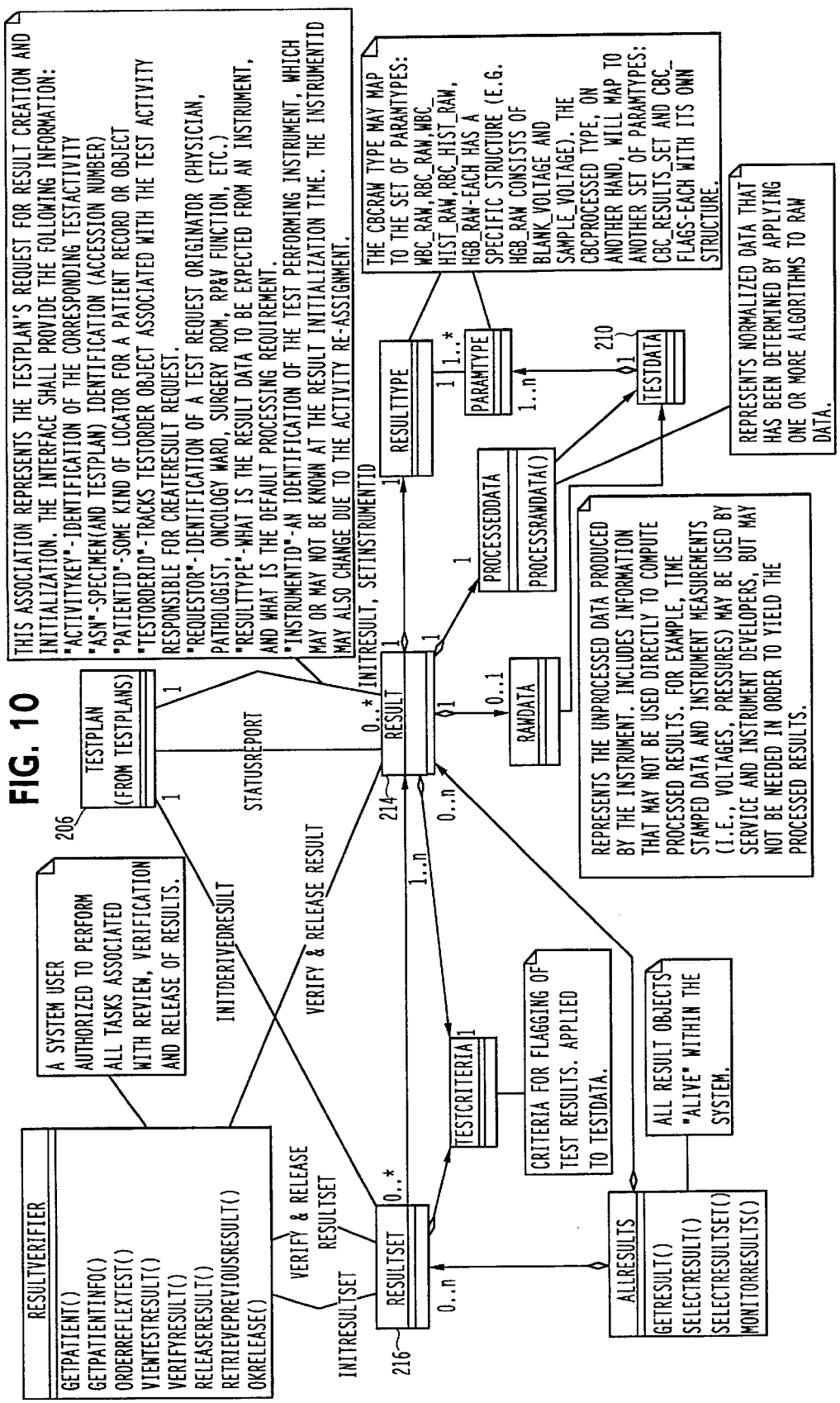
FIG. 10 is a class diagram showing for the results processing and verification category of the invention, a result object support structure and its relationship with the test plan object.
Figure 11:
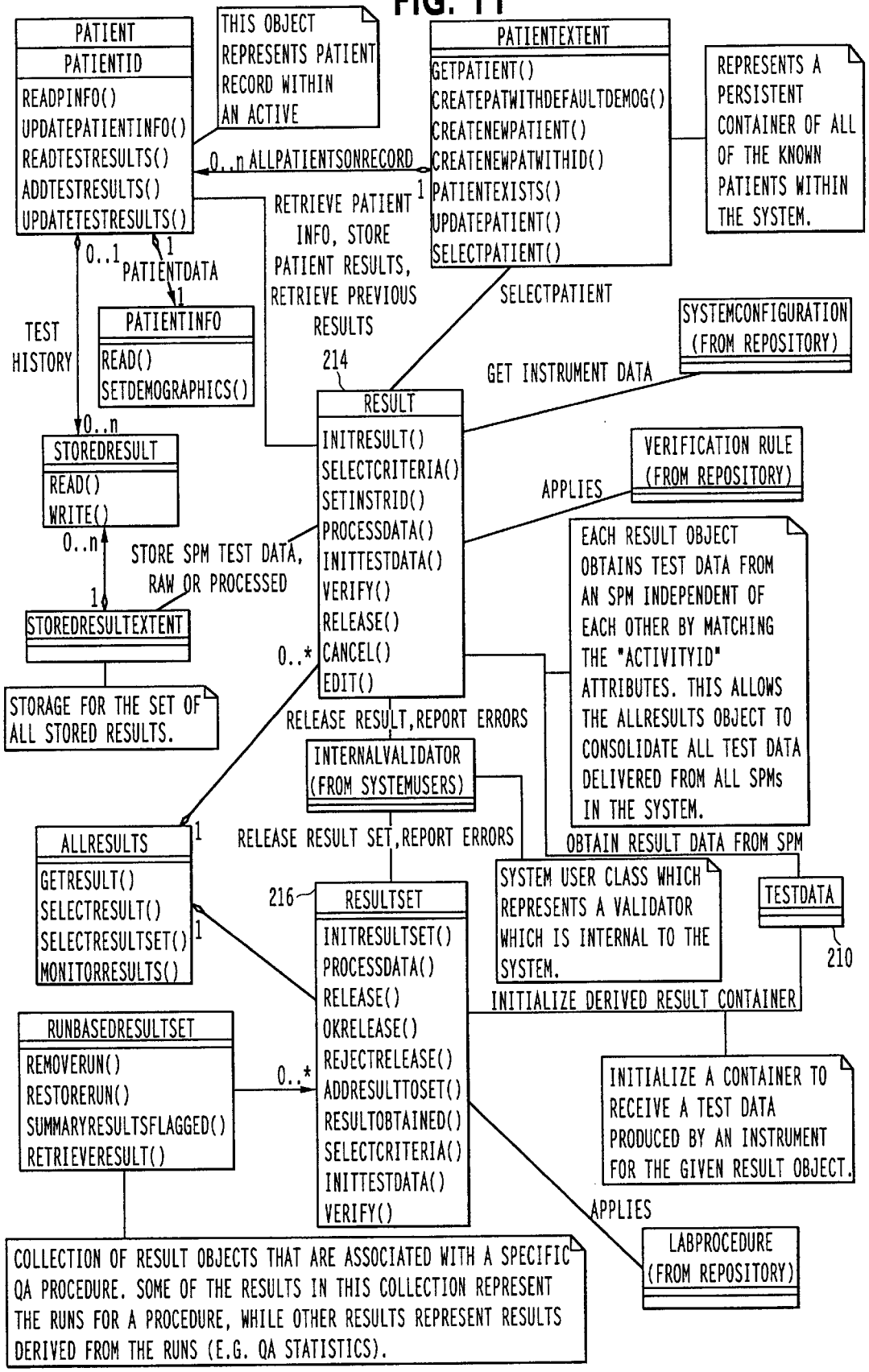
FIG. 11 is a class diagram showing for the results processing and verification category of the invention, the processing of specimen processing module produced data and patient-object relationship.
Figure 12:
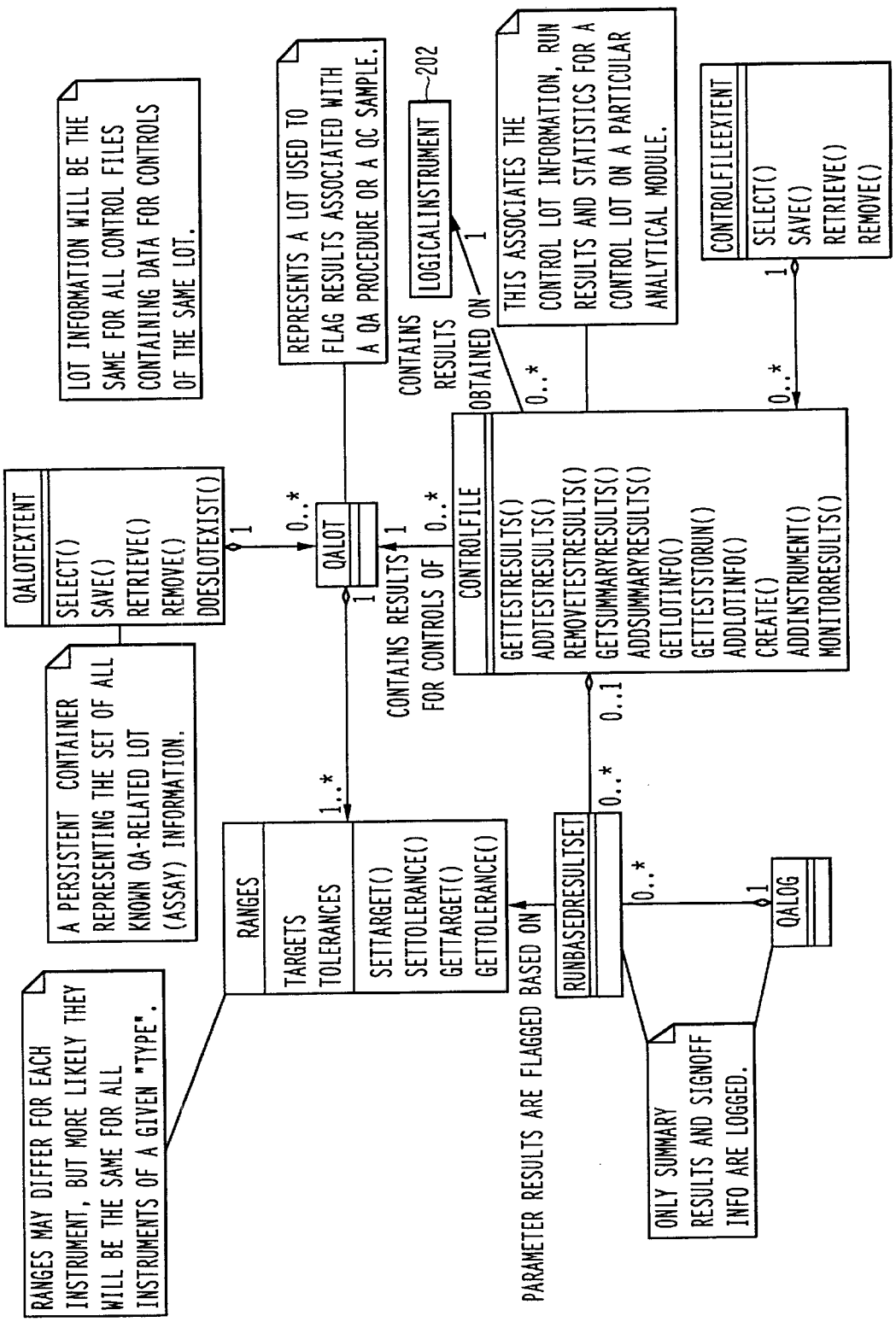
FIG. 12 is a class diagram showing for the results processing and verification category of the invention, a quality assurance procedure support structure for specimen processing module calibration.

FIGS. 10, 11 and 12 provide information on class structure and relationships required to support operations within the results processing and verification category of block 120. The class diagram in FIG. 10 illustrates the main structural elements. FIG. 10 also illustrates the dependency of result objects on objects in the test planning category of block 80. The diagram further illustrates a role of system user objects 226 in verification of results.

FIG. 11 illustrates the dependency between processing SPM produced data and persistent information (e.g. previous patient results, patient demographics, and user defined rules). The class diagram in FIG. 11 emphasizes relationships that target consolidated processing of test data from multiple SPMs, including results verification and release and information exchange with a patient records system.

FIG. 12 shows objects structure and relationships that support SPM calibration tasks within results processing and verification category of block 120. The steps below order a basic set of operations within this category: 1) creating and initializing result objects 214, 2) creating and initializing result set objects 216 (associating result objects 214 by a specified derivation formula or by shared attribute(s)), 3) managing state of result objects 214 and result set objects 216 while supporting status reporting to system user objects 226 (e.g. reporting status of any result or any group of results to an authorized user), 4) assessing processing needs of test data objects 210 (determining type of data supplied by SPM and applicable calibration information, and selecting an algorithm for the processing of the SPM data), 5) determining flagging criteria, applied to result objects 214, and to result set objects 216 (for example, patient demographics and laboratory rules), 6) acquiring test data produced by SPMs and associating it with result objects 214, 7) applying pre-selected algorithms, 8) as required, retrieving previous results for a patient from patient records system, 9) applying flagging criteria, general verification rules and laboratory specific procedures, 10) as required, reporting repeat test or reflex test conditions to system user object, 11) releasing results (release data to a patient records system), 12) deleting result object 214 and result set objects 216.

Figure 26:
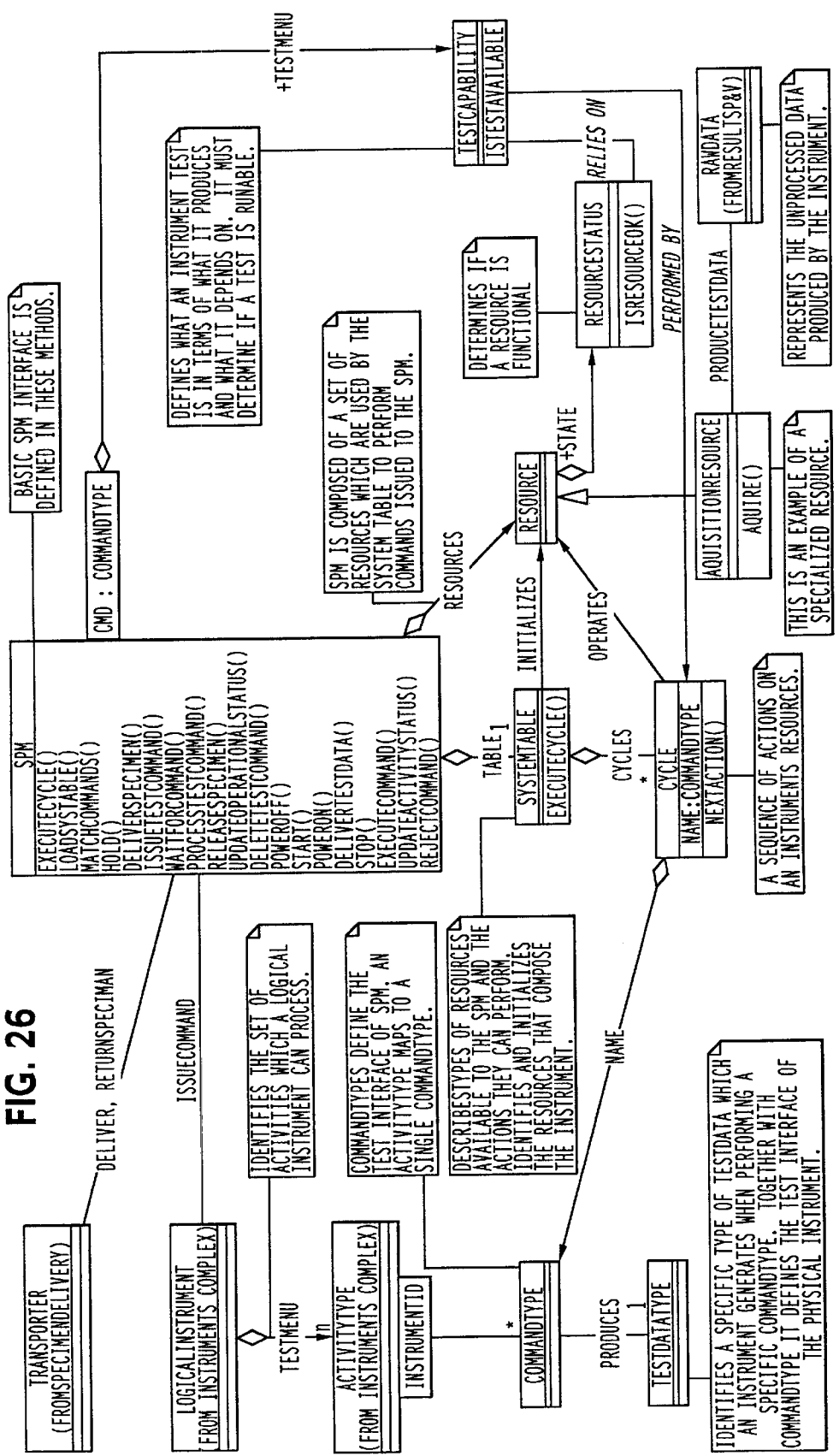
FIG. 26 is a class diagram showing the physical instrument category structure in the invention.

FIG. 26 shows a basic class structure of the physical instrument category of block 140 for a generic hematology instrument. The class structure illustrates some of the requirements for a SPM integration on VIFA based systems.

The description of the structural aspects of the VIFA in FIGS. 4–12 and 26 is supplemented by a description of a common system behavior in FIGS. 13–25. FIGS. 13–25 are object interaction diagrams (OIDs) which present a sequence of operations performed by different objects collaborating in the major aspects of the work flow from the order processing and specimen receipt to results processing and release of test results. The description of system behavior will show how VIFA's internal organization targets automation of laboratory work flow and integrates the four elements of the work flow.

Each OID presents a fragment of a single operational sequence. An operational sequence of submission of test orders, dispatching test activities to SPMs, managing specimen transportation, and processing of results is constructed by grouping the OIDs as shown. Those skilled in the art will appreciate that the OID operational sequence presented is merely exemplary, and the invention is not intended to be limited in this regard.

Figure 13A:
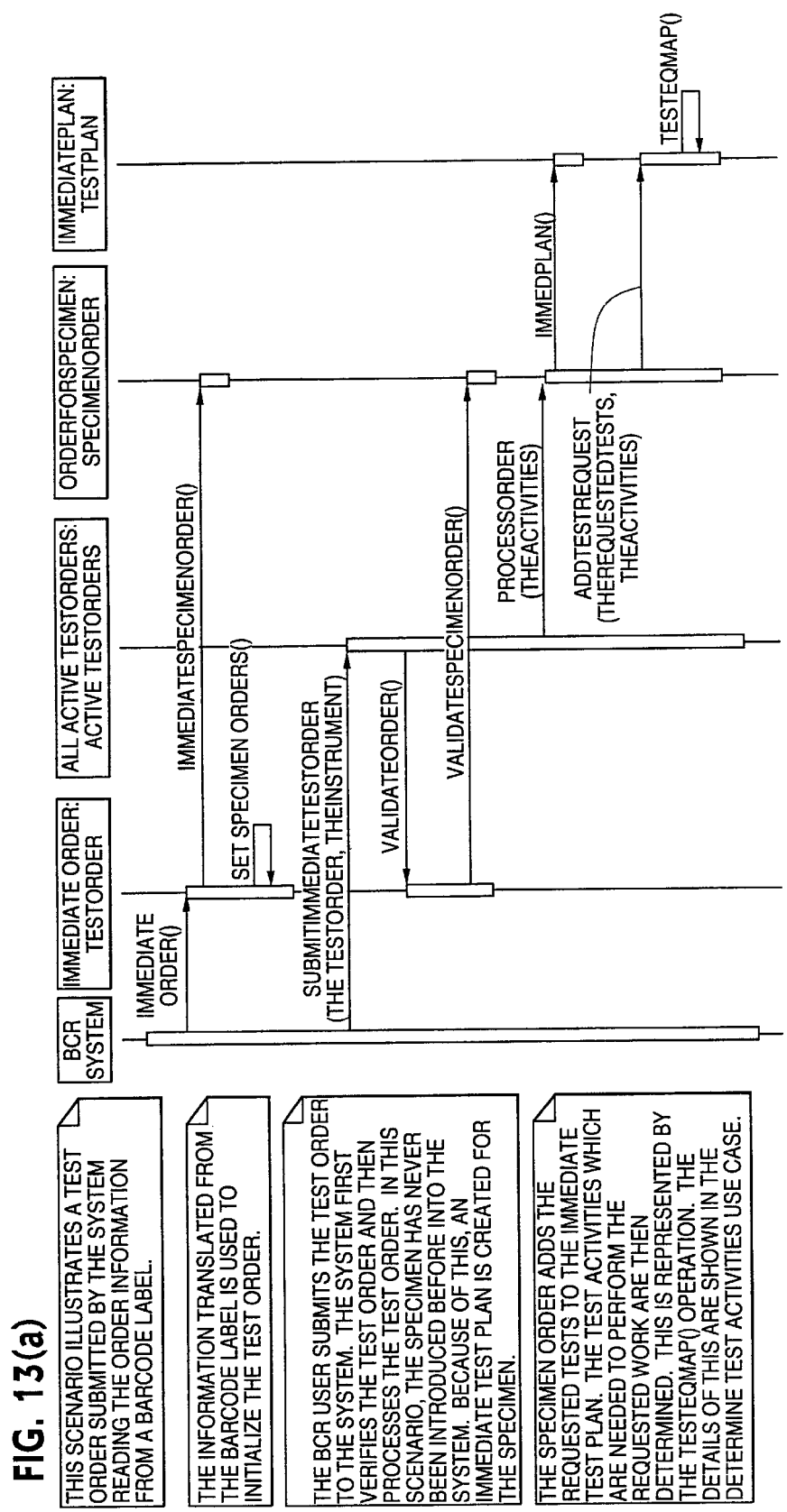
FIGS. 13a and 13b are object interaction diagrams illustrating two scenarios for ordering tests in the invention.
Figure 13B:
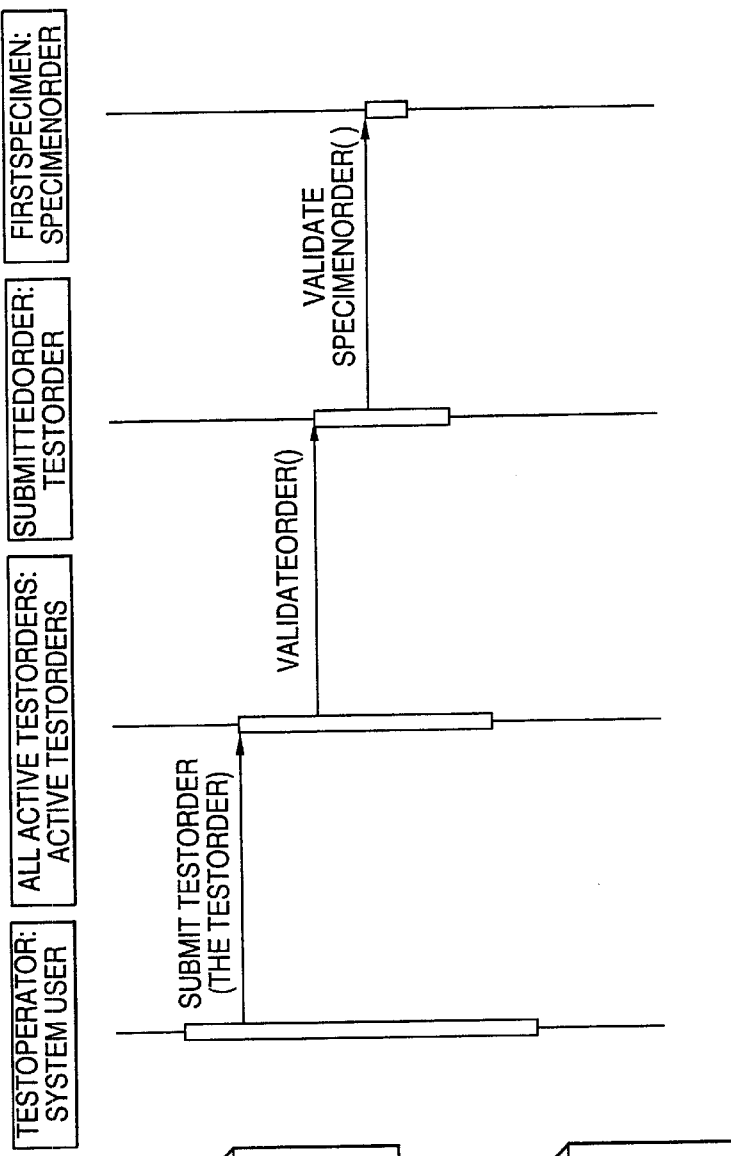
Figure 13C:
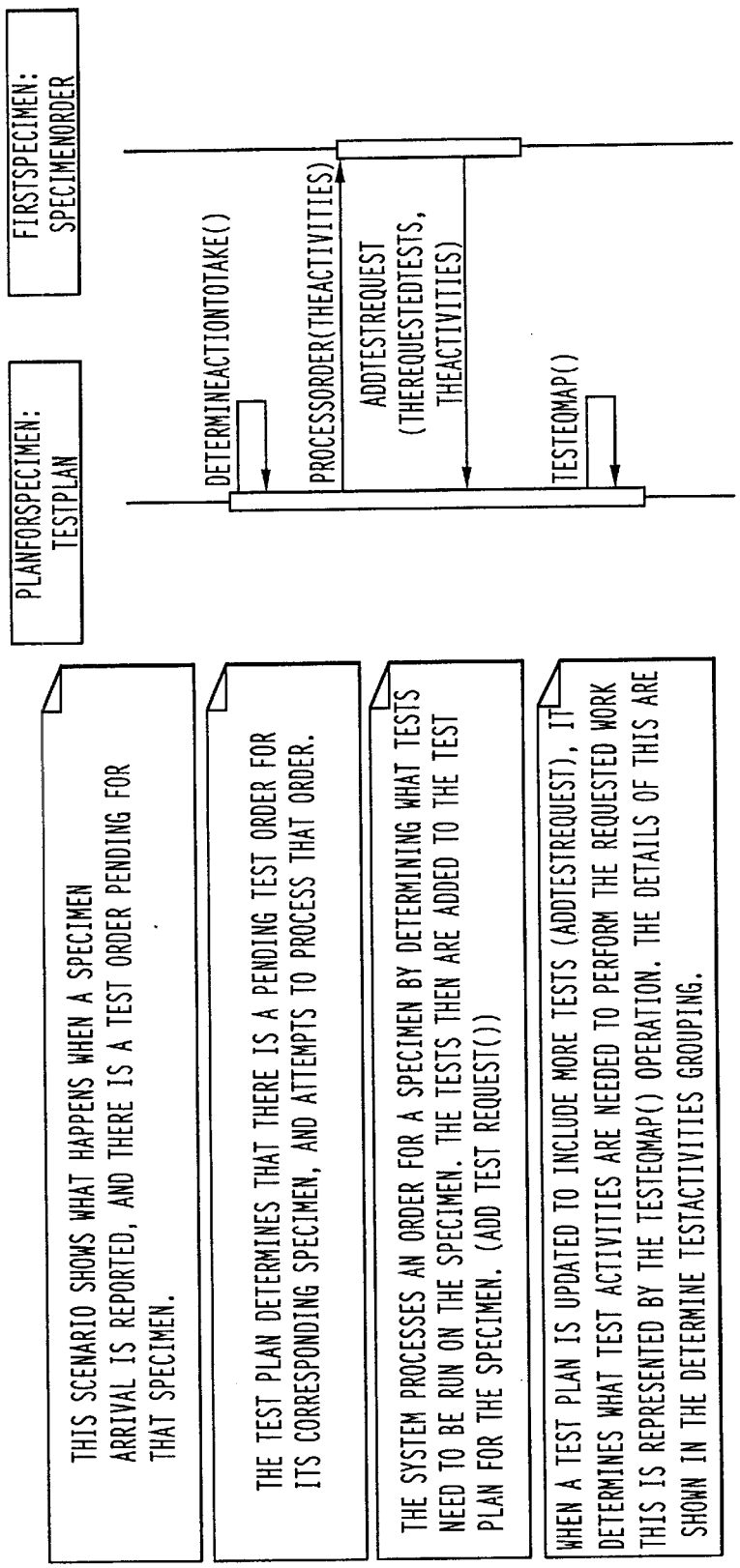
FIG. 13c is an object interaction diagram of the invention illustrating processing of a pending test order.
Figure 16:
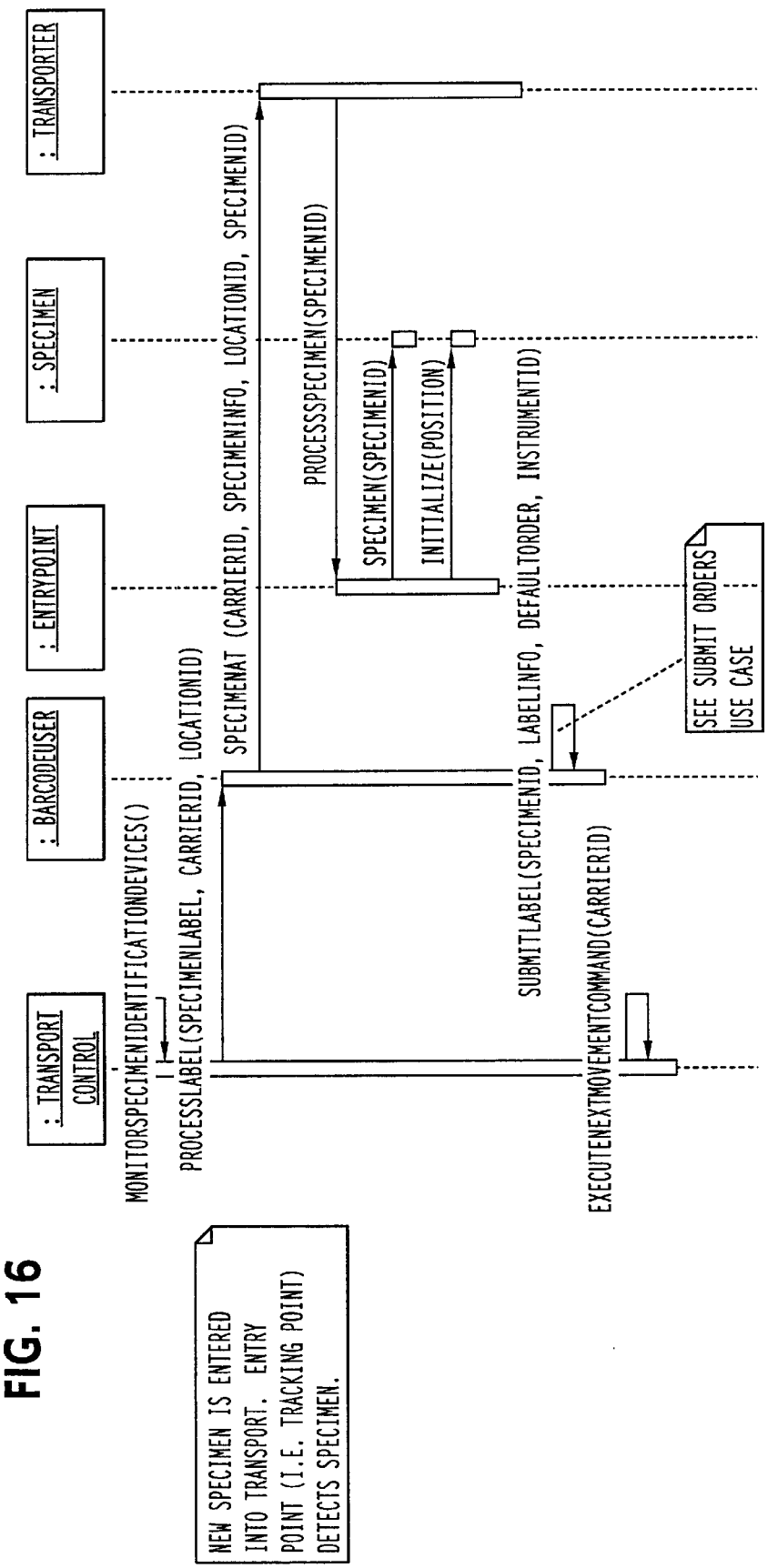
FIG. 16 is an object interaction diagram of the invention illustrating the process of a specimen entering the system.
Figure 17:
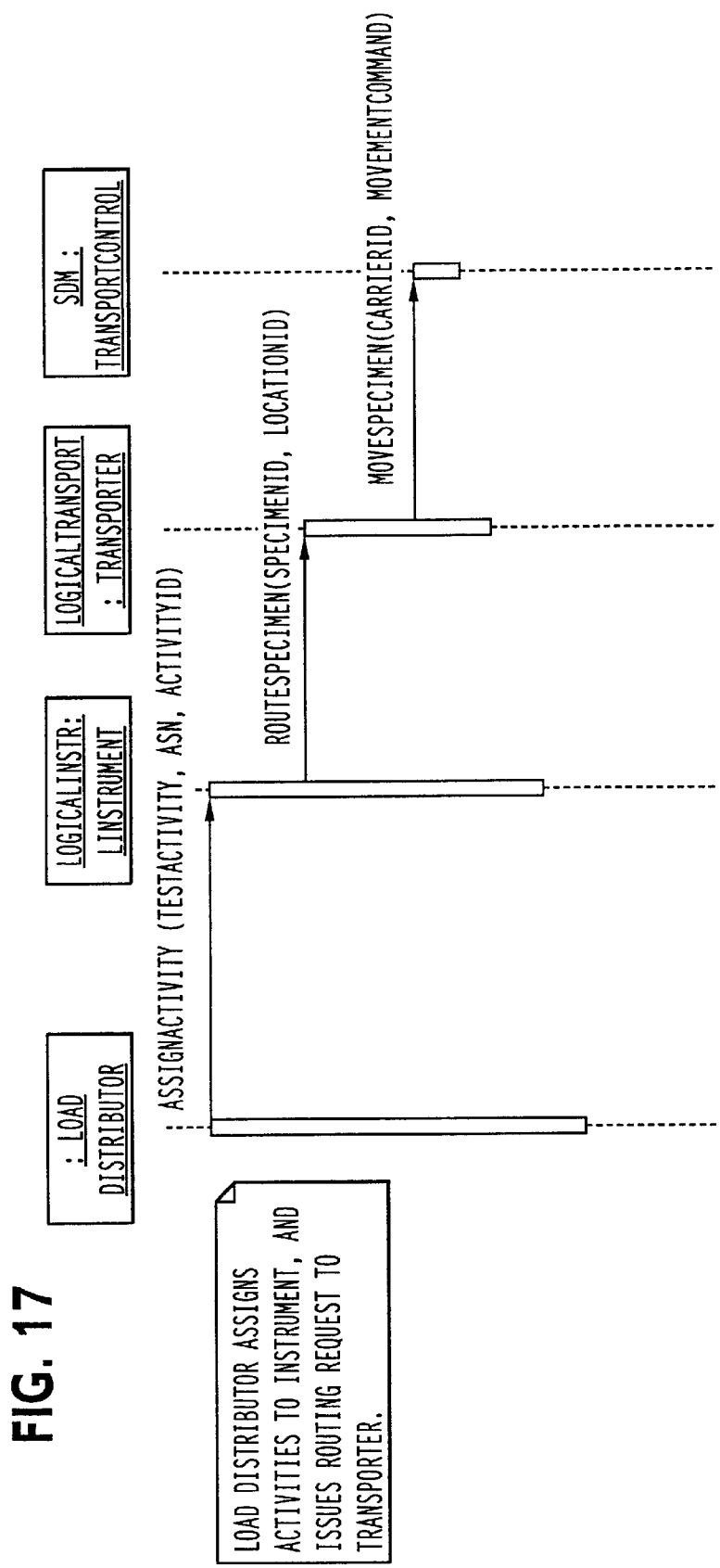
FIG. 17 is an object interaction diagram of the invention illustrating the assignment of test activities to software processing modules and ordering a delivery of a specimen.
Figure 18:
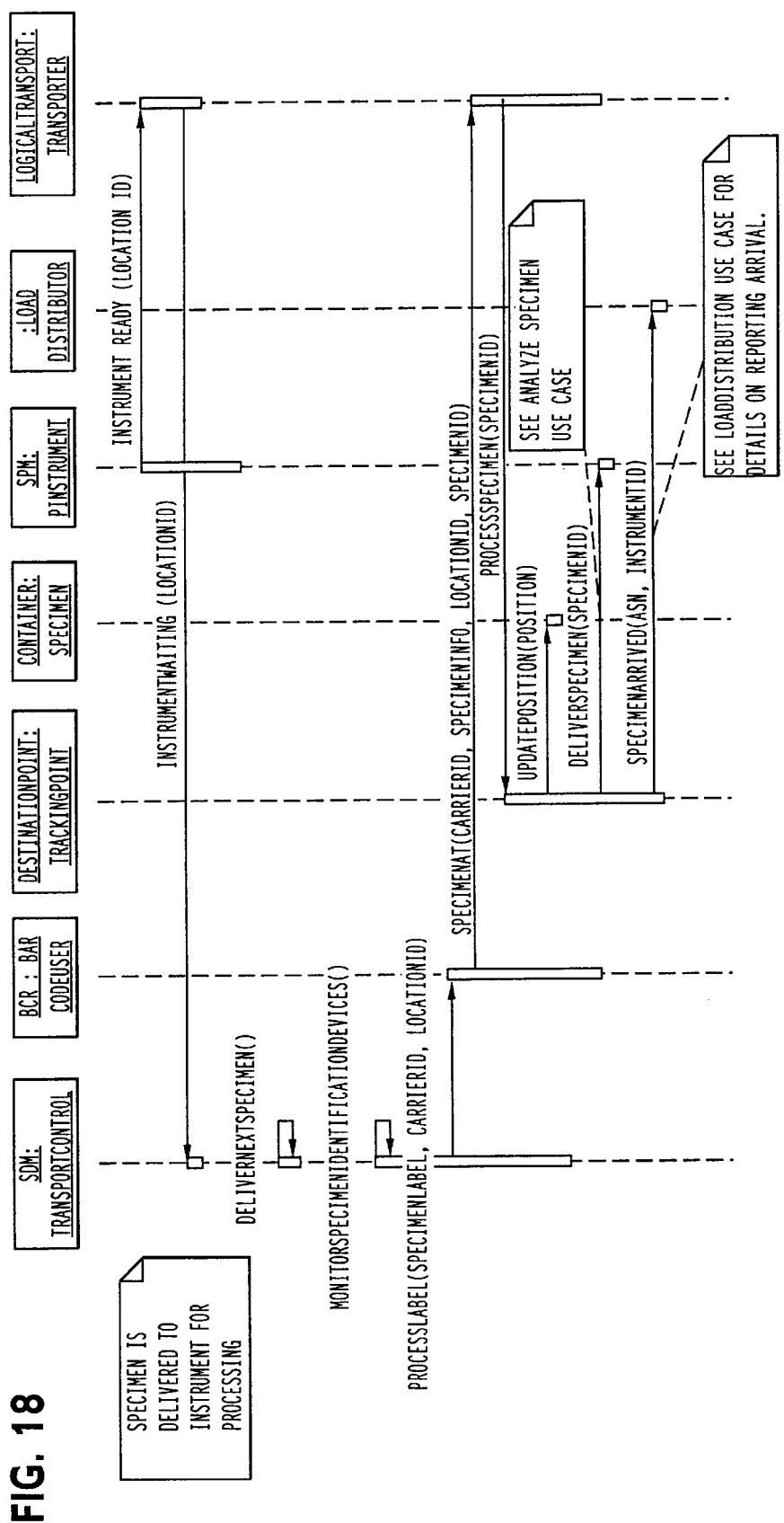
FIG. 18 is an object interaction diagram of the invention illustrating how specimen tracking and delivery is handled after the specimen enters the transport system.
Figure 19:
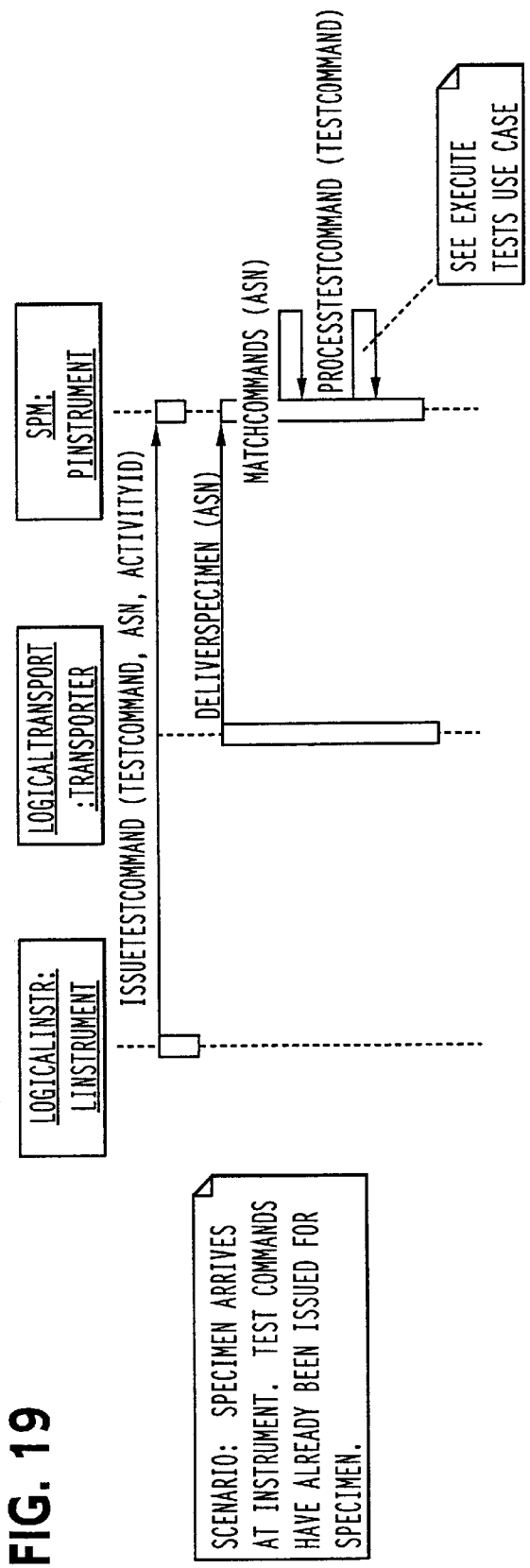
FIG. 19 is an object interaction diagram of the invention illustrating how specimen arrival is handled after the specimen arrives at the specimen processing module.
Figures 20, 21:
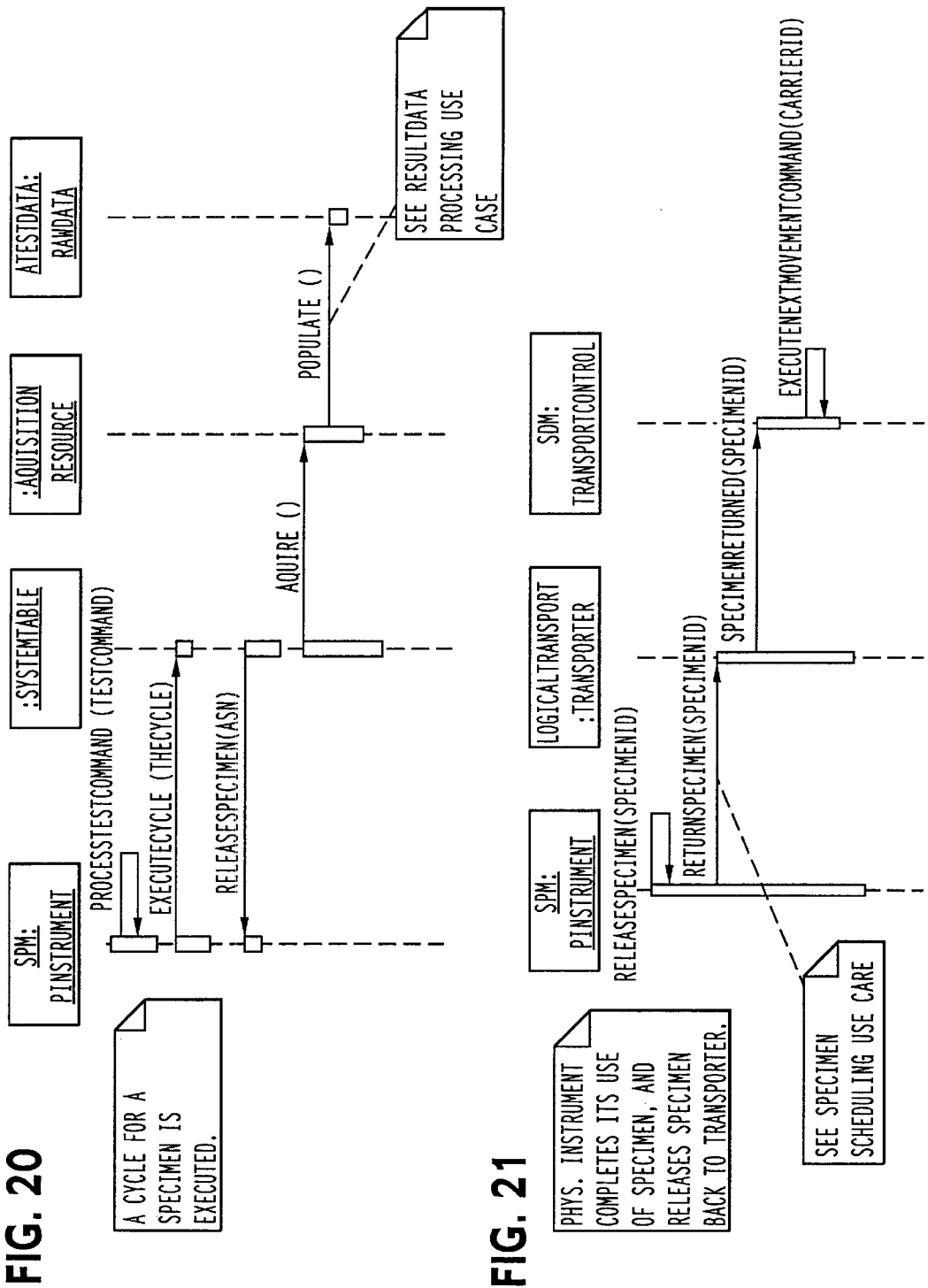
FIG. 20 is an object interaction diagram of the invention illustrating how a specimen is processed after the specimen arrives at the specimen processing module.
FIG. 21 is an object interaction diagram of the invention illustrating how specimen release is handled after the specimen is processed at the specimen processing module.
Figure 25:
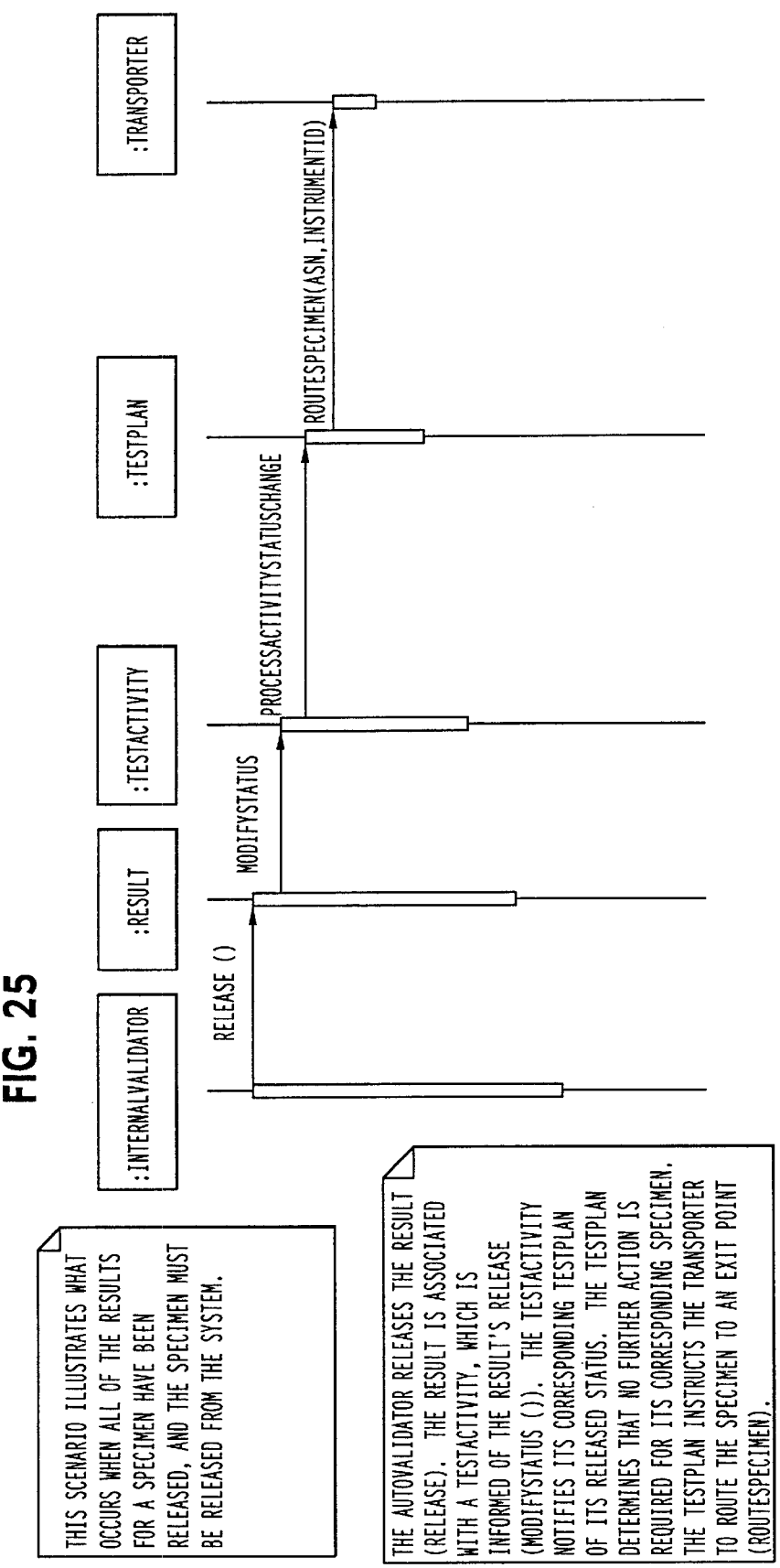

The OIDs in FIGS. 13a–13c illustrate two scenarios for ordering tests in the VIFA based systems. According to one scenario, a test order can be submitted via barcode reading device as follows: 1) a specimen enters the system as shown in FIG. 16; and 2) a test order is submitted by the system user object 226 using the order information from a barcode label on the specimen container (FIG. 13a).

According to a second scenario, the entry of order information and introduction of the specimen can be two separate events. A test order can be submitted before the specimen enters the system. In this case the fragments can be ordered as follows: 1) a test order is submitted from a local or remote workstation (FIG. 13b); 2) a specimen enters the system as shown in FIG. 16 and 3) a pending test order is processed (FIG. 13c). These two scenarios demonstrate differences in behavior depending upon the presence of the specimen at the time of submission of test order.

Figure 15:
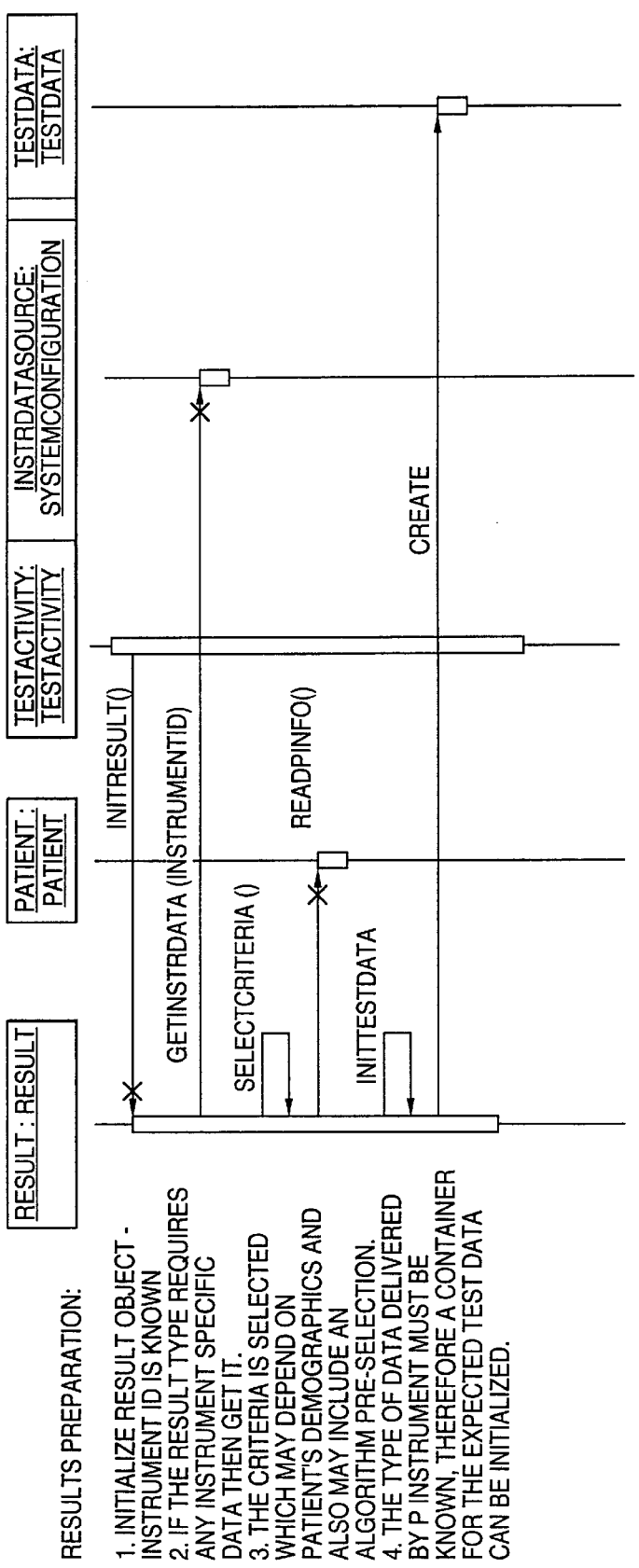
FIG. 15 is an object interaction diagram of the invention illustrating the initialization of result object in order to process and verify the specimen processing module produced test results.

FIG. 14 shows a common fragment of test order processing. This fragment is activated on completion of either scenario from above. Here the collaboration between test plan object 206 and Instrument collection object 220 leads to a selection of test activities, and dispatching the test activities for execution on the instrument complex. As shown in FIG. 15, this process also leads to initialization of result object 214 in order to process and verify the SPM produced test data. The above is followed by assigning test activities to SPM(s) and ordering a delivery of specimen. These operations are shown in the FIG. 17.

The scenario fragments in FIGS. 18, 19, 20 and 21 illustrate how a specimen is handled after entering the transport system. They demonstrate the following basic steps of specimen management: 1) tracking of specimen delivery, 2) specimen arrival at SPM, 3) specimen processing by SPM, and 4) specimen release from SPM.

The scenario fragments in FIGS. 22 to 25 illustrate a basic sequence in which test data delivered by SPMs can be processed, verified and released in the VIFA based systems.

We claim:

1. An extensible clinical laboratory object-based architecture for testing a specimen, comprising:

physical element layer including at least one specimen processing module for performing at least one test on the specimen;

integrated work flow automation layer, provided above the physical element layer, for communicating with said at least one specimen processing module, said work flow automation layer including programming objects which can be specialized including request processing means for processing a user request for any of said tests, functional control means for providing functional control of said at least one specimen processing module for performing any of said tests, and result data management means for processing test result data of any of said tests;

an integrated user interface layer, provided above the integrated work flow automation layer, communicating with said integrated work flow automation layer for permitting a user to control and monitor said software system; and wherein the object-based architecture is extended through published interfaces of the work flow automation layer, and wherein said integrated work flow automation layer has an integrated architecture configured for performing any aspect of pre-analytical, analytical and post analytical laboratory processing of said specimens and said data.

2. The object-based architecture software system according to claim 1 wherein said work flow automation layer is comprised of a plurality of system user objects, each encapsulating a separate user operational category.

3. The object-based architecture according to claim 2 wherein said work flow automation layer is further comprised of:

an order entry and test planning category of objects for permitting any test to be specified, accepted for processing, and scheduled, provided that a specimen processing module having a capability to perform said test is available in said object-based architecture;

an instrument complex category of objects for providing complete management of said at least one specimen processing module; and a result processing and validation category for processing and verifying a result of said tests;

said objects of said order entry and test planning category, said instrument complex category, and said result processing category each communicating with said plurality of system user objects.

4. The object-based architecture according to claim 3 wherein said integrated work flow automation layer further comprises:

a logical transport category of objects to monitor specimen location and to control specimen routing to a selected specimen processing module; and a physical instrument category of objects for representing any type or design of specimen processing module;

said objects of said physical instrument category communicating with said objects of said logical transport category, said instrument complex category and said result processing and validation category for delivering said specimens to said at least one specimen processing module and performing said tests.

5. The object-based architecture according to claim 4 wherein said integrated work flow automation layer further comprises a common infrastructure category of objects communicating with each of said objects of said system users category, results processing and validation category, order entry and test planning category, instrument complex category, logical transport category, and physical instrument category.

6. The object-based architecture according to claim 5 wherein said common infrastructure category of objects implements object distribution, messaging, exception handling, and object persistence.

7. The object-based architecture according to claim 6 wherein said object persistence comprises means for maintaining a database of test result data received from said at least one specimen processing module.

8. The object-based architecture according to claim 5 wherein said at least one plurality of specimen processing module is comprised of instrument hardware and embedded process control software.

9. The object-based architecture according to claim 8 wherein said integrated work flow management layer includes a physical instrument shell which is an external interface configured for enabling integration of any specimen processing module with said integrated work flow management means.

10. The object-based architecture according to claim 2 wherein said plurality of system user objects are comprised of:
   a test operator object for processing user test requests and providing test operation status information for said at least one specimen processing module; and
   an instrument operator object responsive to user commands for controlling operational modes and status for any of said specimen processing modules.

11. The object-based architecture according to claim 10 wherein said plurality of system user objects are further comprised of at least one of the group consisting of:
   a service tech object responsive to user commands for performing service tasks relating to maintenance of said at least one specimen processing module;
   a result verifier object responsive to user commands for manual verification of test result data provided by said at least one specimen processing module; and
   a system administrator object responsive to user requests for managing configuration of said object-based architecture.

12. The object-based architecture according to claim 10 wherein said plurality of system user objects are further comprised of a bar code reader user object responsive to user inputs delivered via bar code reading devices.

13. The object-based architecture according to claim 2 wherein said integrated work flow automation layer further comprises means for verifying medical insurance code data provided for a particular test which has been requested.

14. The object-based architecture according to claim 1, further comprising at least one specimen delivery module for transporting specimens to and from said at least one specimen processing module.

15. The object-based architecture according to claim 14 wherein said work flow automation layer further comprises means for controlling specimen position, routing and distribution to processing sites where said at least one specimen processing module performs said tests.

16. The object-based architecture according to claim 1 wherein said work flow automation layer further comprises means for allocating and scheduling a set of test requests as between different ones of said specimen processing modules when a plurality of requests for tests have been received and are in need of processing.

17. The object-based architecture according to claim 1 wherein said work flow automation layer further comprises means for evaluating compliance of test procedures with quality control requirements.

18. The extensible clinical laboratory object-based architecture of claim 1 wherein
   the integrated work flow automation layer is upwardly scaleable to encompass a plurality of laboratory features, functions or instruments and downwardly scaleable to encompass relatively less laboratory features, functions or instruments.

19. An extensible clinical laboratory object-based architecture for testing a specimen, comprising;
   a set of integrated work flow object classes for communicating with any of a plurality of specimen processing modules for performing any of a plurality of tests;
   an integrated user interface layer, provided above the integrated work flow object classes, communicating with said integrated work flow object classes for permitting a user to control and monitor said object-based architecture; wherein
      said set of integrated work flow object classes including programming objects which can be specialized,
      the object-based architecture is extended through published interfaces of the integrated work flow object classes, and
      said set of integrated work flow object classes having a single integrated architecture configured for providing laboratory information flow management for pre-analytical, analytical and post analytical laboratory processing.

20. The extensible clinical laboratory object-based architecture of claim 19 wherein said object-based architecture is further configured for providing material flow management.

21. The extensible clinical laboratory object-based architecture of claim 20 wherein said object-based architecture is further configured for providing operational, reporting and diagnostic control of said specimen processing modules.

22. The extensible clinical laboratory object-based architecture of claim 21 wherein said object-based architecture is further configured for providing specimen delivery management for coordinating delivery of said specimen to said specimen processing modules.

23. An extensible clinical laboratory framework architecture for testing a specimen, comprising:
   physical element layer including at least one specimen processing module for performing at least one test on the specimen;
   integrated work flow automation layer, provided above the physical element layer, for communicating with said at least one specimen processing module, said work flow automation layer including a core block which isolates the implementation of technology specific software mechanism and programming objects which can be specialized including request processing means for processing a user request for any of said tests, functional control means for providing functional control of said at least one specimen processing module for performing any of said tests, and result data management means for processing test result data of any of said tests;

an integrated user interface layer, provided above the integrated work flow automation layer, communicating with said integrated work flow automation layer for permitting a user to control and monitor said software system; and wherein the framework architecture is extended through published interfaces of the work flow automation layer, and wherein said integrated work flow automation layer has an integrated architecture configured for performing any aspect of pre-analytical, analytical and post analytical laboratory processing of said specimens and said data.

* * * * *